US009322761B2

(12) United States Patent
Miller

(10) Patent No.: US 9,322,761 B2
(45) Date of Patent: Apr. 26, 2016

(54) METHODS AND APPARATUS FOR ASCERTAINING INTERFERENTS AND PHYSICAL DIMENSIONS IN LIQUID SAMPLES AND CONTAINERS TO BE ANALYZED BY A CLINICAL ANALYZER

(75) Inventor: Kerry L. Miller, Elkton, MD (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 179 days.

(21) Appl. No.: 13/389,761

(22) PCT Filed: Aug. 5, 2010

(86) PCT No.: PCT/US2010/044515
§ 371 (c)(1),
(2), (4) Date: Feb. 9, 2012

(87) PCT Pub. No.: WO2011/019576
PCT Pub. Date: Feb. 17, 2011

(65) Prior Publication Data
US 2012/0140230 A1   Jun. 7, 2012

Related U.S. Application Data

(60) Provisional application No. 61/274,199, filed on Aug. 13, 2009.

(51) Int. Cl.
G01N 21/00        (2006.01)
G01N 15/04        (2006.01)
(Continued)

(52) U.S. Cl.
CPC .............. *G01N 15/042* (2013.01); *G01N 15/05* (2013.01); *G01N 21/25* (2013.01); *G01N 35/00603* (2013.01); *G01N 2015/045* (2013.01); *G01N 2015/055* (2013.01)

(58) Field of Classification Search
CPC ....... G01N 21/55; G01N 21/27; G01N 21/25; G01F 23/292; G01F 23/2928
USPC .................. 356/441–442, 409, 436
See application file for complete search history.

(56) References Cited

U.S. PATENT DOCUMENTS 3,489,525 A * 1/1970 Natelson ................. 422/64
5,336,467 A * 8/1994 Heidt et al. ............. 422/64
(Continued)

FOREIGN PATENT DOCUMENTS

EP          1425590 B1    11/2006
JP     Hei 04-130248 A     5/1992
(Continued)

OTHER PUBLICATIONS

Japanese Office Action of corresponding Japan patent Application No. 2012-524750, 9 Pages.
(Continued)

*Primary Examiner* — Tarifur Chowdhury
*Assistant Examiner* — Isiaka Akanbi
(74) *Attorney, Agent, or Firm* — Dugan & Dugan, PC

(57) ABSTRACT

A method of inspecting a clinical specimen for a presence of one or more interferents, such as those that might be found within clinical analytical blood specimens by subjecting the specimen to centrifugation to separate the specimen into a red blood cell portion and a blood serum or plasma portion is provided. Subsequent to the centrifuging procedure, the serum or plasma portion of the clinical analytical specimen may be tested for the presence of one or more interferents such as hemolysis, icterus, lipemia, or liquid nonuniformities therein. Additionally, physical dimensional characteristics of the sample container and/or specimen may be determined. Apparatus for carrying out the method are described, as are other aspects.

21 Claims, 10 Drawing Sheets

(51) Int. Cl.
*G01N 15/05* (2006.01)
*G01N 21/25* (2006.01)
*G01N 35/00* (2006.01)

(56) References Cited

U.S. PATENT DOCUMENTS

| | | | |
|---|---|---|---|
| 5,422,712 A | 6/1995 | Ogino | |
| 5,602,647 A * | 2/1997 | Xu et al. | 356/435 |
| 6,353,471 B1 | 3/2002 | Samsoondar et al. | |
| 6,388,750 B1 | 5/2002 | Liu et al. | |
| 6,628,395 B2 * | 9/2003 | Liu et al. | 356/436 |
| 6,882,425 B1 * | 4/2005 | Elsenhans et al. | 356/436 |
| 7,061,605 B2 | 6/2006 | Lemmo et al. | |
| 7,473,897 B2 | 1/2009 | Braendle et al. | |
| 8,144,328 B2 * | 3/2012 | Venugopal et al. | 356/437 |
| 2002/0098528 A1 * | 7/2002 | Gordon et al. | 435/7.21 |
| 2002/0122364 A1 * | 9/2002 | Worthington et al. | 369/47.35 |
| 2005/0036146 A1 * | 2/2005 | Braig et al. | 356/436 |
| 2005/0243303 A1 * | 11/2005 | Pettersson et al. | 356/39 |
| 2007/0190637 A1 | 8/2007 | Samsoondar | |
| 2008/0283781 A1 | 11/2008 | Carter et al. | |
| 2008/0297769 A1 | 12/2008 | Bamberg et al. | |
| 2011/0164124 A1 * | 7/2011 | Hizume et al. | 348/61 |

FOREIGN PATENT DOCUMENTS

| | | |
|---|---|---|
| JP | Hei 06-043090 A | 2/1994 |
| JP | Hei 10-019885 A | 1/1998 |
| JP | 2000-227399 A | 8/2000 |
| JP | 2004-037322 A | 2/2004 |
| JP | 2005-156329 A | 6/2005 |
| JP | 2007-263907 A | 10/2007 |
| JP | 2008-519604 A | 6/2008 |
| JP | 2009-036511 A | 2/2009 |

OTHER PUBLICATIONS

Partial Supplementary EP Search Report dated Jan. 11, 2016 of corresponding European Application No. 10808551.5, 3 Pages.

* cited by examiner

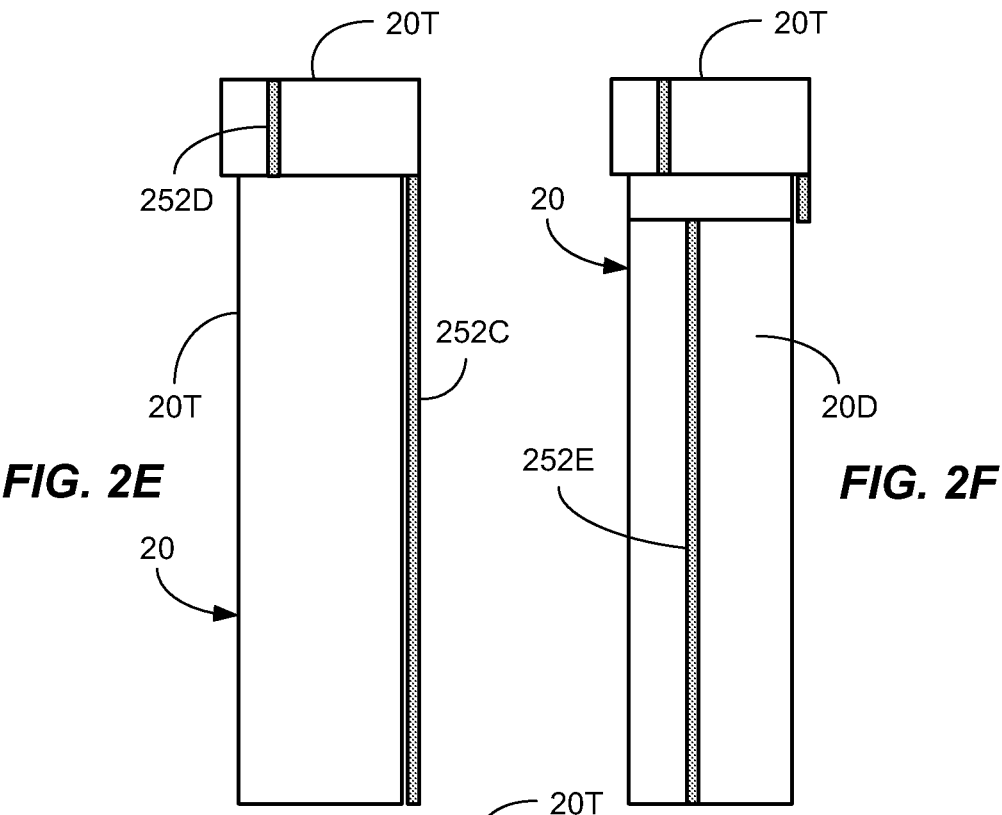
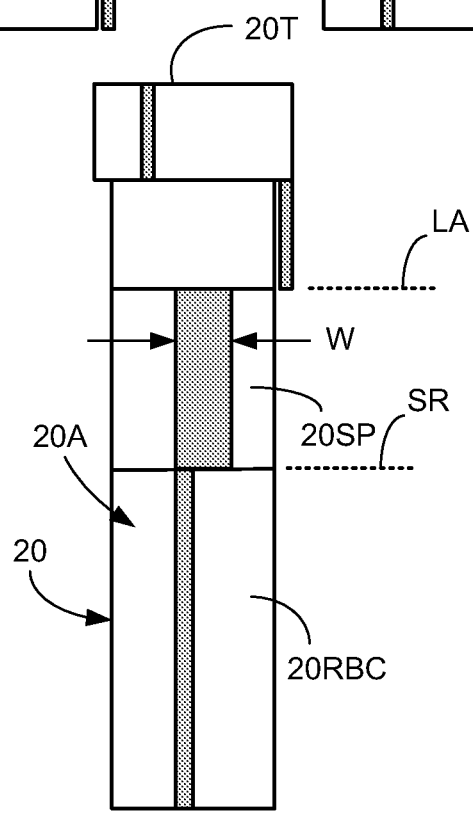

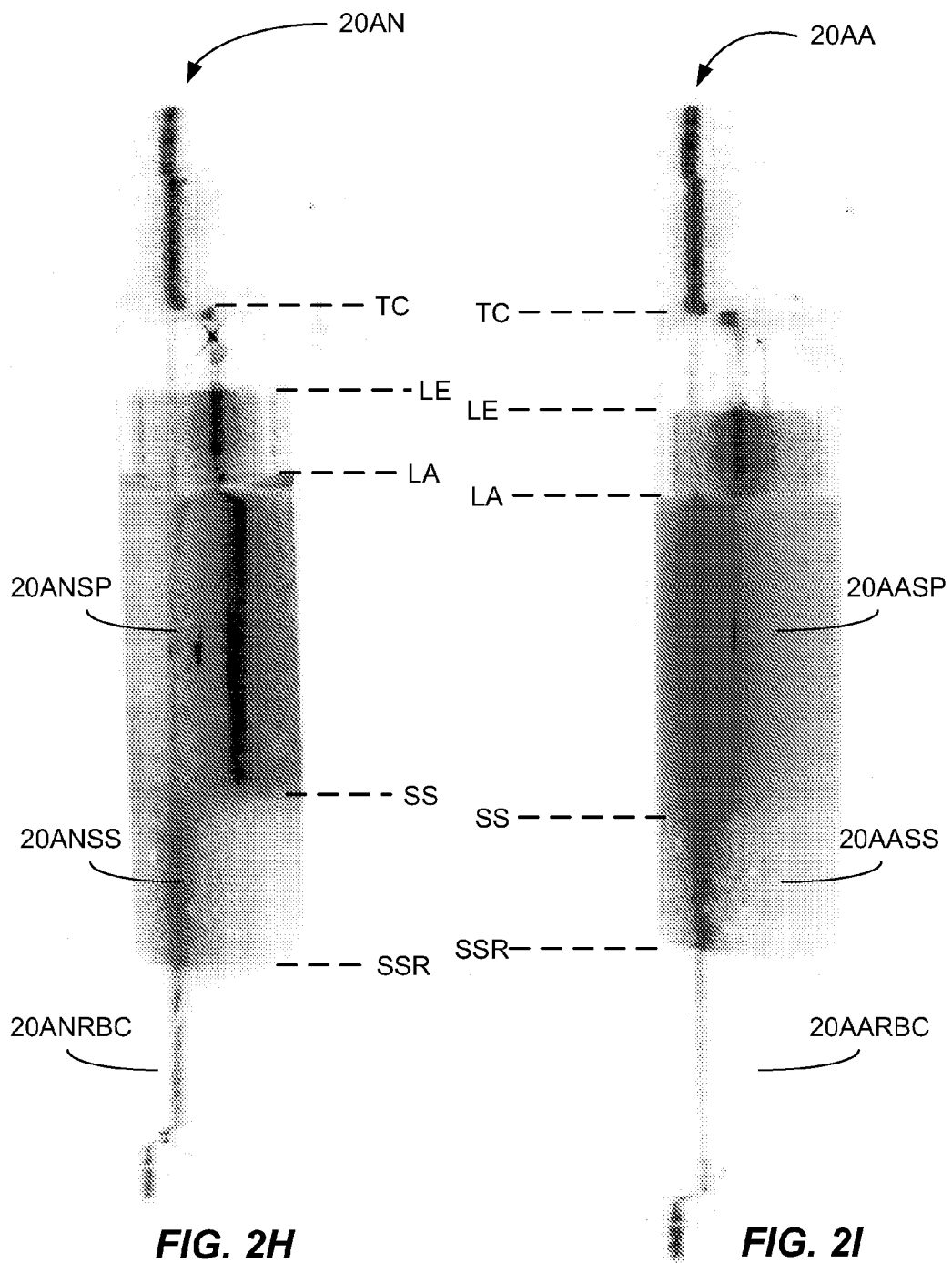
*FIG. 2H*  *FIG. 2I*

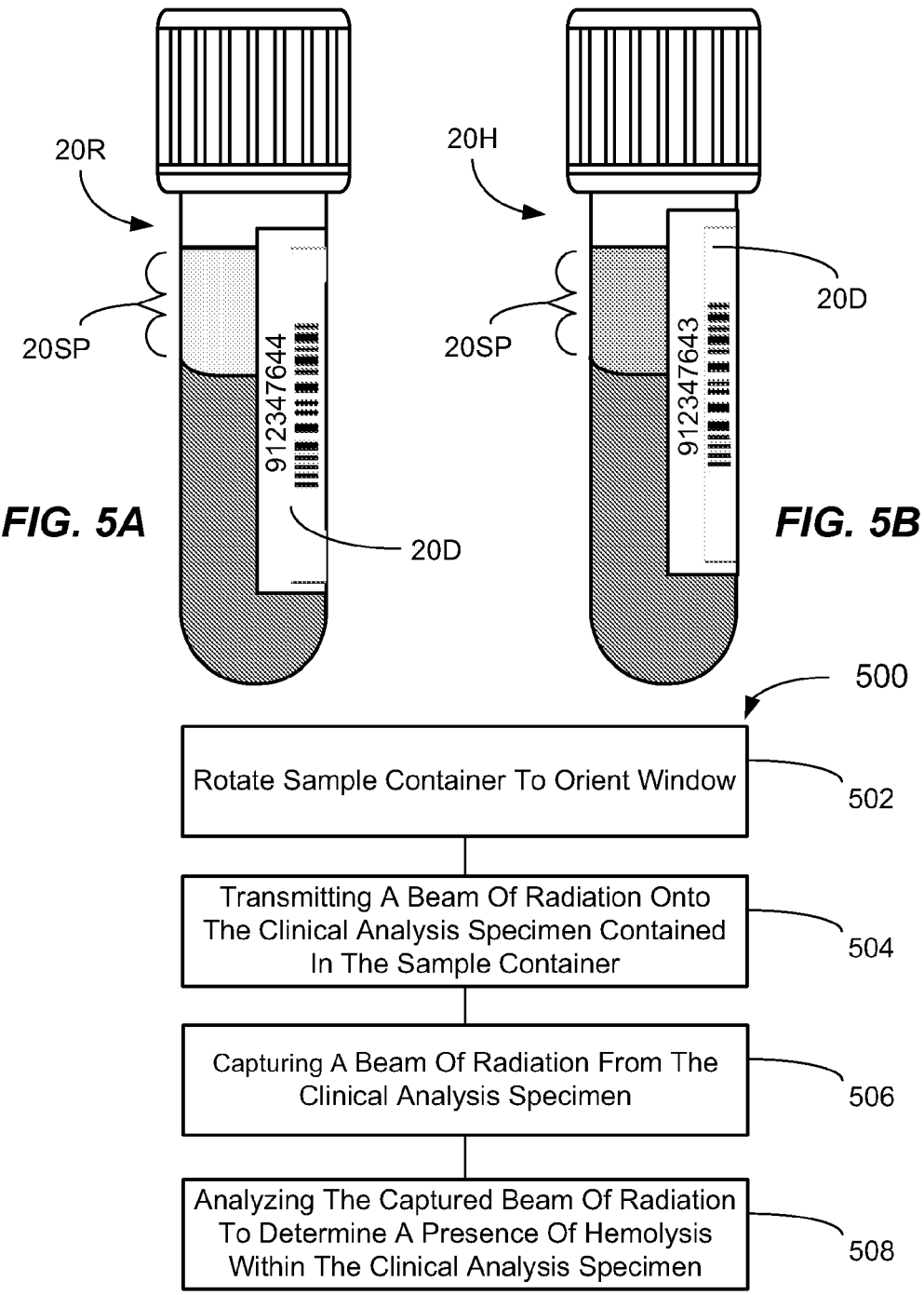

METHODS AND APPARATUS FOR ASCERTAINING INTERFERENTS AND PHYSICAL DIMENSIONS IN LIQUID SAMPLES AND CONTAINERS TO BE ANALYZED BY A CLINICAL ANALYZER

RELATED APPLICATIONS

This application claims priority to U.S. Provisional Application Ser. No. 61/274,199 entitled "Method And Apparatus For Ascertaining Interferents In Liquid Samples To Be Analyzed By A Clinical Analyzer" filed on Aug. 13, 2009, the disclosure of which is hereby incorporated by reference in its entirety herein.

FIELD OF THE INVENTION

The present invention relates to methods and apparatus for testing of liquid samples and, more particularly, to methods and apparatus for determining a presence of a component in the liquid samples.

BACKGROUND

A wide variety of automated chemical analyzers are known in the art and are continually being improved to increase analytical menu and throughput, to reduce turnaround time, and to decrease requisite sample volumes. These clinical analyzers may conduct assays using reagents to identify analytes in a biological fluid sample such as urine, blood serum, plasma, cerebrospinal liquids, and the like. For convenience and safety reasons, these fluid samples are almost universally contained within capped sample containers (e.g., sample tubes). The assay reactions generate various signals that may be manipulated to determine a concentration of analyte in the sample. See, for example, U.S. Pat. Nos. 7,101,715 and 5,985,672 assigned to the assignee of the present application and incorporated herein by reference. Improvements in clinical analyzer technology have been accompanied by corresponding advances in pre-analytical sample preparation and handling operations such as sorting, batch preparation, centrifugation of sample tubes to separate sample constituents, cap removal to facilitate fluid access, and the like by automated pre-analytical sample preparation systems called Laboratory Automation Systems (LASs). LASs automatically transport sample in sample tubes to a number of pre-analytical sample processing stations that have been "linked together" like described in U.S. Pat. Nos. 6,984,527 and 6,442,440, both incorporated herein by reference.

These LASs may handle a number of different patient specimens contained in standard, bar code-labeled, and evacuated sample tubes. The bar code label may contain an accession number that may be coupled and correlated to demographic information that may be entered into a hospital's Laboratory Information System (LIS) along with test orders and other desired information. An operator may place the labeled sample containers (e.g., tubes) onto the LAS system, which may automatically sort and route the sample tubes to the requisite processing devices for pre-analytical operations such as centrifugation, decapping, and aliquot preparation prior to the specimen being subjected to clinical analysis by one or more analytical stations that may also be "linked" to the LAS.

For certain clinical assays, a serum or plasma portion (obtained from whole blood by centrifugation) may be used in the clinical analysis. To prevent clotting, an anticoagulant such as citrate or heparin may be added to the blood specimen immediately after it is originally obtained. Alternatively, the anticoagulant may be placed in an empty sample container (e.g., tube) prior to the patient sample being obtained. At a later time, the specimen may be centrifuged to separate the serum or plasma portion from the red blood cell portion. A serum separator may be added to the sample container to aid in the separation of the red blood cell portion from the serum or plasma portion.

After centrifuging and a subsequent de-capping process, the open sample container (e.g., tube) may be transported to an appropriate clinical analyzer that may extract liquid specimen from the sample container and combine the specimen with one or more reagents in special reaction containers (e.g., cuvettes or cups). Analytical measurements may then be performed, often using a beam of interrogating radiation interacting with the sample-reagent combination, for example, by using photometric or fluorometric absorption readings or the like. The measurements allow determination of end-point or rate values from which an amount of analyte related to the health of the patient may be determined using well-known calibration techniques. Unfortunately, the presence of certain components (e.g., colored interferents) in the sample as a result of some preexisting sample condition or processing may adversely affect the accuracy of the results of the analyte measurement obtained from the clinical analyzer.

In some cases, the integrity of the serum or plasma portion of the specimen may affect the interpretation of the results, i.e., the analyte reading of the clinical analyzer. For example, pre-analytical variables in the serum or plasma portion, which are not related to the patient disease state, may cause a different interpretation of the disease condition of the patient. Pre-analytical variables include hemolysis (ruptured red blood cells), icterus (excessive bilirubin), and lipemia (high, visible lipid content).

Typically, the integrity of the serum or plasma portion of the specimen is visually inspected by a skilled laboratory technician. This may involve a review of the color of the serum or plasma portion of the specimen. A normal serum or plasma portion has a light yellow to light amber color. Alternately, a serum or plasma portion containing hemolysis may be quite reddish in color. Interferents may arise, for example, if an excess number of red blood cells are damaged, possibly during venipuncture, centrifugation, or after prolonged storage. When red blood cells are injured, they release low density, reddish-colored hemoglobin into the specimen causing a reddish-colored sample that is said to exhibit "hemolysis." The presence of free hemoglobin (Hb) may be used to measure the degree of hemolysis and, when the hemoglobin concentration exceeds about 20 mg/dl, the hemoglobin may interfere with the colorimetric determination of analytes in the clinical analyzer due to the reddish interferent contained in the specimen.

A sample containing icterus may be dark yellow/brown in color. Such interferents may arise, for example, from an excess of bilirubin, the result of decaying red blood cells being converted in the spleen into bilirubin. Levels of bilirubin above 2-3 mg/dl are visibly yellowish and may, in particular, adversely affect enzyme-based immunoassays. Such a condition is termed bilirubinaemia or icterus.

A sample containing lipemia may be whitish in color. Interferents may arise, for example, as a whitish appearance in serum or plasma portion due to the presence of excess lipids. Such a condition is called lipemia and lipid levels above about 50 mg/dl may interfere with antibody binding in immunoassays and may accordingly also affect immunoassay results.

Thus, the degree of red color in a serum sample may correspond to the amount of hemolysis present in the serum or plasma portion of the specimen, the degree of dark yellow/brown color may correspond to the amount of icterus present in the serum or plasma portion of the specimen, and the degree of whitish color may correspond to the amount of lipemia present in the serum or plasma portion of the specimen.

Subsequent to centrifugation, when the red blood cell portion has been separated from the serum or plasma portion, a skilled technician may visually inspect the serum or plasma portion and, if judged to not have a normal light yellow to light amber color, the specimen may be discarded. Otherwise, the specimen will be processed and analyzed as ordered. However, visual inspection is very subjective, labor intensive, and fraught with the possibility of human error. Thus, various methods have been implemented to ascertain whether hemolysis, icterus, and lipemia (these three conditions are frequently called "HIL") are present in a serum or plasma portion of the specimen.

Typically, a laboratory technician will assign a hemolytic index, an icteric index, and a lipemic index to the serum and plasma portion of the specimen based upon the color. Based upon the value of the hemolytic index, the icteric index, and the lipemic index, the interpretation of the results from the clinical analyzer can be evaluated. Alternately, if the value of one or more of the hemolytic index, the icteric index, and the lipemic index are too high, the specimen may be discarded without analysis by the clinical analyzer.

As mentioned above, visual inspection can be labor intensive and costly. Furthermore, the possibility of human error exists with visual inspection, the results of the visual inspection may be highly subjective and may vary between workers, and one variable could mask or hide other variables. Furthermore, with closed container sampling, bar code labels directly on the container, and the use of automated clinical analyzers, the laboratory technician, in many instances, may simply not have a clear opportunity to visually observe the serum or plasma portion of the specimen. Thus, it is becoming increasingly important to evaluate the integrity of the serum or plasma portion of the specimen without the use of visual inspection by a laboratory technician.

One attempt to solve this problem involves optically viewing the serum or plasma portion of the specimen after the serum or plasma portion has been transferred to one of the cuvettes of the clinical analyzer. Measuring the optical characteristics of the specimen in the clinical analyzer eliminates the need for visual inspection. However, this test utilizes machine time of the clinical analyzer and, if the integrity of the specimen is determined to be compromised, additional machine time and a machine cycle are wasted. Furthermore, this procedure cannot be used with clinical analyzers that add reagents to the cuvette prior to adding the serum or plasma portion of the specimen.

U.S. Pat. No. 5,734,468 discloses monitoring a serum sample with a detector that performs a spectrophotometric analysis of the serum sample in the probe lumen through a substantially transparent section of the probe. From the spectrophotometric analysis, a hemolytic index, an icteric index, and a lipemic index of the serum sample can be established. Based upon these serum indices, the serum sample can be transferred to a clinical analyzer for additional tests or can be disposed of because the sample is compromised.

U.S. Pat. No. 6,372,503 discloses quality control material used to monitor instrument calibrations or used for recalibration for instruments that assess the amount of hemolysis, turbidity, bilirubinemia, and biliverdinemia, either separately, or any two, or any three, or all four simultaneously, in plasma or serum samples.

U.S. Pat. No. 6,628,395 discloses preliminarily testing a sample for HIL in the original incoming sample container, prior to being removed from the container and prior to being transferred to a clinical analyzer. In this approach, sample is not consumed and can be transferred to the clinical analyzer or a waste receptacle based upon results of the evaluation.

U.S. Pat. No. 6,353,471 discloses a method to reject a sample from further analysis based on determining the concentration of at least one interferent in the sample by: (1) irradiating the sample with at least one frequency of radiation; (2) correlating absorbance of the radiation by the sample with a standard for the interferent(s) to determine the concentration of the interferent(s), and (3) rejecting the sample if the concentration of the interferent(s) exceeds a predetermined criteria.

One challenge in performing spectrophotometric analysis has been that the specimens are initially obtained in a variety of primary patient sample collection containers ("sample containers"). These sample containers are usually tubes of varying diameters and lengths. In the case of a patient blood sample, the liquid is often centrifuged to separate the liquid serum or plasma portion from the cellular phase (e.g., red blood cell portion). Such sample containers may have a patient identification label, varying and unpredictable amounts of the serum or plasma portion to be analyzed in the total specimen, and contain a relatively large amount of sample liquid.

Because of the problems encountered when endogenous interferents are contained within liquid samples to be clinically analyzed, there is an unmet need for a method and apparatus adapted to determine a presence of such interferents. The method and apparatus should not appreciably adversely affect the speed at which analytical test results are obtained and should allow making a determination on a relatively large sample portion so that the accuracy of such a determination is not affected. Furthermore, the method and apparatus should be able to be used even on labeled sample containers.

SUMMARY OF THE INVENTION

According to a first aspect of the invention, a method of determining a characteristic of a clinical analysis specimen contained within a sample container is provided. The method includes transmitting a beam of radiation through the clinical analysis specimen contained within the sample container; capturing a beam of radiation transmitted through the sample container; and analyzing the captured beam of radiation to determine a presence of one or more interferents within the clinical analysis specimen.

According to another aspect of the invention, a method of determining a characteristic of a clinical analysis specimen contained within a sample container is provided. The method includes transmitting a beam of radiation through the sample container; capturing a beam of radiation transmitted through the sample container; and analyzing the captured beam of radiation to determine a physical dimensional characteristic of the clinical analysis specimen.

According to another aspect of the invention, a method of determining a characteristic is provided. The method includes transmitting a beam of radiation through the sample container adapted to contain a clinical analysis specimen; capturing a beam of radiation transmitted through the sample container;

and analyzing the captured beam of radiation to determine a physical dimensional characteristic of the sample container.

According to another aspect of the invention, an apparatus adapted to determine a characteristic of a clinical analysis specimen contained within a sample container is provided. The apparatus includes a radiation source adapted to transmit a beam of radiation through the clinical analysis specimen contained within the sample container; a radiation capture device adapted to capture a beam of radiation as transmitted through the sample container; and a computer adapted to analyze the captured beam of radiation to determine a presence of one or more interferents within the clinical analysis specimen.

According to another aspect of the invention, a method adapted to determine a characteristic of a clinical analysis specimen contained within a sample container is provided. The method includes transmitting a beam of radiation onto the clinical analysis specimen contained within the sample container; capturing a beam of radiation reflected by the clinical analysis specimen; and analyzing the captured beam of radiation to determine a presence of one or more interferents within the clinical analysis specimen.

In another aspect of the invention, a method adapted to determine a characteristic of a clinical analysis specimen contained within a sample container is provided. The method includes transmitting a beam of radiation onto the sample container; capturing a beam of radiation reflected by the clinical analysis specimen in the sample container; and analyzing the captured beam of radiation to determine a physical dimensional characteristic of the clinical analysis specimen.

Another aspect of the invention provides a method adapted to determine a physical characteristic of the sample container. The method includes providing a sample container adapted to contain a clinical analysis specimen; transmitting a beam of radiation onto the sample container; capturing a beam of radiation reflected by the sample container; and analyzing the captured beam of radiation to determine a physical dimensional characteristic of the sample container.

According to yet another aspect of the invention, a method adapted to determine a characteristic is provided. The method includes transmitting a beam of radiation onto a sample container containing a clinical analysis specimen; capturing a beam of radiation reflected by the clinical analysis specimen in the sample container; and analyzing the captured beam of radiation to determine at least one selected from a group consisting of a physical dimensional characteristic of the clinical analysis specimen, a physical dimensional characteristic of the sample container, and a presence of an interferent within the clinical analysis specimen.

In another aspect of the invention, an apparatus for analyzing a clinical analysis specimen contained within a sample container is provided. The apparatus includes a radiation source adapted to transmit a beam onto the clinical analysis specimen contained within the sample container; a radiation capture device positioned to capture a beam of radiation reflected by the sample container; and a computer adapted to analyze the captured beam of radiation to determine a presence of one or more interferents within the clinical analysis specimen.

According to yet another aspect of the invention, a method of determining a characteristic of a clinical analysis specimen contained within a sample container is provided. The method includes transmitting a beam of radiation at the clinical analysis specimen contained within the sample container; capturing a beam of radiation transmitted through the sample container or reflected from the clinical analysis specimen; and analyzing the captured beam of radiation to determine a presence of one or more interferents within the clinical analysis specimen, wherein the one or more interferents is selected from a group consisting of lipemia, hemolysis, and icterus.

Still other aspects, features, and advantages of the present invention may be readily apparent from the following detailed description by illustrating a number of exemplary embodiments and implementations, including the best mode contemplated for carrying out the present invention. The present invention may also be capable of other and different embodiments, and its several details may be modified in various respects, all without departing from the spirit and scope of the present invention. Accordingly, the drawings and descriptions are to be regarded as illustrative in nature, and not as restrictive. The drawings are not necessarily drawn to scale. The invention is to cover all modifications, equivalents, and alternatives falling within the spirit and scope of the invention.

BRIEF DESCRIPTION OF THE DRAWINGS

FIGS. 2E-2G are schematic side views of images of light reflections for various specimen and sample container conditions generated by the sample quality station of FIG. 2A.

FIGS. 2H-2I are actual side view images of light reflections for various specimen and sample container conditions generated by the sample quality station of FIG. 2A.

FIG. 5A is an illustration of a sample container containing a reference specimen.

FIG. 5B is an illustration of a sample container having a specimen with an elevated amount of hemolysis above a pre-established threshold.

FIG. 5C is a flowchart illustrating a method of detecting hemolysis according to an aspect of the present invention.

DEFINITIONS

Figure 1A:
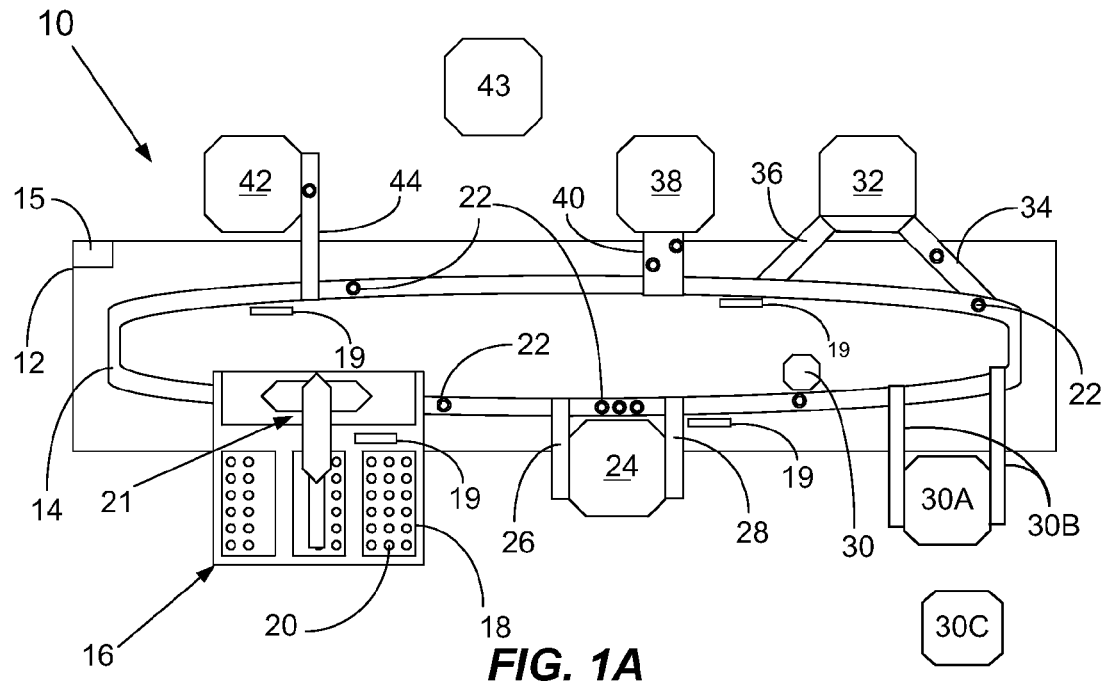
FIG. 1A is a schematic top plan view of an automated sample handling system including a conveyor controlled in cooperation with one or more pre-analytical sample quality stations and analytical stations in which the present invention may be employed advantageously.

The following terms used in this application shall have the following meaning:

"Sample Tube" shall mean a blood collection tube used to collect blood from a patient. However, the sample tube may include any structural configuration adapted to receive and contain blood, such as tubular, slightly conical, etc. Additionally, the sample tube may be used for the initial collection of the blood from the patient or the blood may be transferred to the sample tube after being collected in another container. A suitable blood collection tube is manufactured by Becton Dickinson, located in Franklin Lakes, N.J.

"Serum Variables" shall mean and include hemolysis, icterus, lipemia, and other variables in the serum or plasma portion that may affect the accuracy of results of a clinical analyzer.

"Interferent" shall mean and include any of the serum variables, any disease condition, and/or any opacity, coloration, or particulate that may affect the interpretation of results of a clinical analyzer.

"Hemolytic index" shall mean the grade given to a particular sample based upon the estimated content of hemolysis present in the sample (specimen). Generally, the grading scale for visual observation ranges from zero through four (0-4). Zero represents substantially no hemolysis while four represents significant hemolysis. Alternately, the scale could be 0-10, 0-20, A-F, or some other range.

"Icteric index" shall mean the grade given to a particular sample based upon the estimated content of icterus present in the sample (specimen). Generally, the grading scale for visual observation ranges from zero through four (0-4). Similarly, zero represents substantially no icterus, while four represents significant presence of icterus. Alternately, the scale could be 0-10, 0-20, A-F, or some other range.

"Lipemic index" shall mean the grade given to a particular sample based upon the estimated content of lipemia present in the sample (specimen). Generally, the grading scale for visual observation ranges from zero through four (0-4). Similarly, zero represents substantially no lipemia, while four represents significant presence of lipemia. Alternately, the scale could be 0-10, 0-20, A-F, or some other range.

"Serum Indices" shall mean and include the hemolytic index, the icteric index, and the lipemic index.

"Predetermined Value" shall mean a value for the hemolytic index, the icteric index, or the lipemic index at which the integrity of the sample for testing may be considered to be compromised. The predetermined value varies according to the scale of the serum indices, which of the serum indices is in question, and the tests to be performed by the clinical analyzer or other device. For example, if the hemolytic index is rated on a scale of 0-4, a hemolytic index of 3 could be considered to compromise the sample for some tests. Thus, the predetermined value in this example would be 3. Alternately, a reading of 2 on a scale of 0-4 for the icteric index could be unacceptable in some instances. Thus, for this example, the predetermined value is 2.

"Spectrophotometric analysis" shall mean and include measuring optical absorbance and/or reflectance, a turbidimetric analysis, a nephelometric analysis, and/or light scatter analysis at any angle or collection of angles. In general, the term "spectrophotometric" refers to capturing spectral response over a range of wavelengths and correlating a response for each of the wavelengths. A device that performs this analysis is referred to as a "spectrophotometer." Such spectrophotometric analysis has been performed with near-infrared and adjacent visible radiation, which is capable of ascertaining hemoglobin, glucose, albumin, lipoproteins, and many other sera components.

DETAILED DESCRIPTION

In a first broad aspect, the present invention provides methods and apparatus for determining if analytical interferents are present in a liquid specimen. The method may be carried out as a pre-analysis step prior to the liquid sample (specimen) being presented to a clinical analyzer for analytical analysis. In particular, one aspect of the present invention provides for delivering centrifuged samples for analytical analysis subsequent to being pre-inspected for a presence of an interferent like those that might be found within a blood sample. This aspect is accomplished by subjecting a liquid blood sample to an appropriate centrifugation to separate the sample into a red blood cell portion, and a blood serum or plasma portion. Subsequent to this centrifuging procedure, the blood serum or plasma portion of the sample (specimen) is tested for the presence of an interferent, such as hemolysis, icterus, and/or lipemia (hereinafter HIL) or other liquid non-uniformities therein (e.g., improper supernat level). If the sample is found to be free of interferents, it is allowed to continue through the system to be routinely processed for analytical analysis.

In one aspect, if the sample is found to contain more than a predefined amount of lipemia, then the sample may be rejected. The lipemic sample may then be subjected to a special pre-processing operation adapted to reduce an amount of lipemia therein. The specimen may then be allowed to be routinely processed for analysis or possibly retested for the presence of an interferent. In another aspect, if the specimen is found to contain more than a predefined amount of hemolysis, then the sample may be allowed to continue and be routinely processed for analytical analysis. However, the extent or degree of hemolysis may be reported along with the analytical results. Alternatively, the hemolyzed specimen may be subjected to a more sophisticated determination of the amount of hemolysis so that any analytical tests to be conducted on the specimen that are not affected by the presence of hemolysis may be routinely completed, and possibly a redraw of a fresh sample may be ordered and undertaken. If the specimen is found to contain more than a predefined amount of icterus, then the specimen may be allowed to be routinely processed for analytical analysis and the extent or degree of icteria may be reported along with the analytical results. The invention is based on the discovery that the extent of scatter or "bloom" of a collimated light beam directed through a centrifuged sample is a more rapid and less complex determination of a presence of an interferent (e.g., lipemia) in the specimen than other more sophisticated methods.

These and other aspects and features of the invention will be described with reference to FIGS. 1A-7 herein.

FIG. 1A shows an automated clinical chemistry sample handling system 10 (hereinafter "automated sample handling system") capable of automatically pre-processing multiple sample containers 20, typically sample tubes (e.g., test tubes or blood collection tubes—see FIG. 1B), contained in multiple sample racks 18 prior to analysis by a clinical analyzer 32, 38, and/or 42. However, any generally clear or transparent container may be used, such as a sample cup, cuvette, or other clear glass or plastic container. Typically, the clinical analysis specimens 20A (hereinafter "specimens") to be automatically processed may be provided to automated sample handling system 10 in the sample containers 20, which may be capped with a cap 20B. Each of the sample containers 20 (e.g., sample tubes) may be provided with identification indicia and/or information 20C, such as a bar code, alphabetic, numeric, or alphanumeric indicia, that may be machine readable by one or more sensors 19. The indicia and/or information 20C may indicate a patient's identification as well as the assay procedures to be accomplished upon the clinical analysis specimen 20A therein, for example. Such indicia and/or information 20C may be generally provided on a label 20D adhered to, or otherwise provided on the side of, the sample container 20. Such labels 20D generally do not extend all the way around the sample container 20. Accordingly, a window is provided along a side of the sample container 20 where the label 20D is not located and the clinical analysis specimen 20A may be viewed from the side in or through this window without interference by the label 20D. The sample containers 20 may be held in racks 18 that may have additional identification indicia thereon.

Automated sample handling system 10 may include an operating base 12 (e.g., a frame) upon which a conveyor track 14 (which may be belt-like) or other suitable conveyance mechanism or system transports individual sample containers 20 (e.g., sample tubes) carried in sample container carriers 22 from a sample container loading/unloading robotic station 16, having one or more racks 18 as well as active input lanes, to a centrifuge 24 (e.g., an automated centrifuge). After being centrifuged, the sample containers 20 may continue on conveyor track 14 to a sample quality station 30 described hereinafter and adapted for automatically determining a presence of one or more interferents in the specimens 20A to be automatically processed by the automated sample handling system 10. The specimens 20A may then be analyzed in the one or more analyzers 32, 38, and/or 42 before returning each sample container 20 (e.g., sample tube) to the sample container loading/unloading robotic station 16. It should be understood that more than three analyzers 32, 38, and 42 may be linked by the conveyor track 14 but, for purposes of simplicity, only three are shown. Additionally, a remote analyzer 43 may be serviced by automated sample handling system 10 even though the remote analyzer 43 is not directly linked to the automated sample handling system 10. For instance, an independent robotic system may carry specimens to the remote analyzer 43. The automated sample handling system 10 may include a number of sensors (not shown) at one or more locations for detecting a location of sample containers 20 by means of reading identifying indicia or information (not shown) placed within each sample tube carrier 22. In some embodiments, a distinct RFID chip may be embedded in each sample tube carrier 22 and conventional RFID reader systems may be employed in such tracking operations, for example.

Centrifuge 24 and each analyzer 32, 38, and 42 may be generally equipped with various robotic mechanisms 26 and 28, 40 and 44, or tracks 34 and 36, respectively, for removing a sample tube carrier 22 from the track 14, moving the sample tube carrier 22 to and from centrifuge 24, to and from the analyzers 32, 38, and 42, or facilitating movement of a sample container 20 into and out of the analyzers 32, 38, and 42. Typically, the loading/unloading station 16 may include at least two X-Y-Z robotic arms 21 conventionally equipped with robotic clamping hands or fingers. However, any suitable robotic apparatus may be used.

Automated sample handling system 10 may be controlled by a conventionally-programmed computer 15, preferably a microprocessor-based central processing unit CPU, which may be housed as part of, or separate from, the automated sample handling system 10. The conventionally-programmed computer 15 may operate to control movement of the sample tube carriers 22 to and from the sample container loading/unloading robotic station 16, the centrifuge 24, quality control station 30, and each clinical analyzer 32, 38, 42 (whereat various types of assay processing occurs) as described below. Computer 15 may control the automated sample handling system 10 according to software, firmware, or hardware commands or circuits such as those used on the Dimension® clinical chemistry analyzer sold by Siemens Healthcare Diagnostics Inc. of Deerfield, Ill., and such control is typical to those skilled in the art of computer-based electromechanical control programming. However, any suitable electronic component or system for controlling the automated sample handling system 10 may be used.

The present invention may be implemented using a computer interface module (CIM) that allows for a user to easily and quickly access a variety of control screens and status information display screens. These screens may describe some or all aspects of a plurality of interrelated automated devices used for sample preparation and clinical analysis of a patient's specimen. Such a CIM preferably employs a first display screen that is directly linked to a plurality of additional display screens containing on-line information about the operational status of a plurality of interrelated automated devices as well as information describing the location of any specific sample and the status of clinical tests to be performed on the sample. The CIM is thus adapted to facilitate interactions between an operator and automated sample handling system 10 wherein the CIM may include a visual touch screen adapted to display a menu including icons, scroll bars, boxes, and buttons through which the operator may interface with the automated sample handling system 10 and wherein the menu comprises a number of function buttons programmed to display functional aspects of the automated sample handling system 10.

In the instance described hereinabove wherein analyzer 32 is, for example, a clinical chemistry analyzer 32 and analyzer 38 is a coagulation analyzer, different centrifuge protocols may be established within centrifuge 24 in order to provide a properly centrifuged and pre-assay treated sample for testing by the chemistry analyzer 32 or by the coagulation analyzer 38. As previously mentioned, sample containers 20 may be provided with identification indicia or information 20C readable by sensor 19 indicating the assay procedures to be accomplished upon the sample therein. Computer 15 is programmed to determine whether an assay is a clinical chemistry analysis or a coagulation analysis and which analyzers 32, 38, and 42 are adapted to perform such analyses.

FIG. 10 is schematic plan view of a first embodiment of an apparatus which may be used at a sample quality station 30 of FIG. 1A and which may be adapted for automatically determining a presence of one or more interferents in a specimen 20A to be automatically processed by the automated sample handling system 10 of FIG. 1A. The presence of the interferent may be detected by the sample quality station 30 prior to being further tested by the automated sample handling system 10. In this manner, if the specimen 20A includes an interferent, additional processing, discarding, or a redraw may take place. Additionally, other detection methods may take place on the analysis specimen 20A contained in the sample container 20, as well as on the sample container 20 itself. For example, the apparatus may be used to determine certain physical dimensional characteristics of the specimen (e.g., the liquid-air interface LA, location of the interface SR between the red blood cell portion 20RBC and the serum or plasma portion 20SP, a height of the red blood cell portion $H_{RBC}$, and a height of the serum plasma portion $H_{SP}$, as shown in FIG. 1 B) and/or certain physical dimensional characteristics (e.g., height H or width W) of the sample container 20 (e.g., of the sample tube) or the location of the tube/cap interface TC.

Now referring to FIG. 10, sample quality station 30 may comprise a radiation source 52 (e.g., a collimated light source), for example. The radiation source 52 may be a laser diode, which directs a laser beam 52A of coherent light onto the sample container 20 (e.g., sample tube). The sample container 20 may be supported upon a rotating holder 54, which may be a table or platform or other rotating apparatus adapted to support and hold the sample container 20 in a generally upright condition during rotation. Appropriate laser diodes for the radiation source 52 are well known in the art and include, inter alia, He, Ne, Gas, GAAS diodes. A radiation capture device 56, such as a conventional digital camera, a charged coupled device (CCD), or a spectrophotometer, may in some embodiments capture a beam of radiation transmitted through sample container 20. The captured image of the transmitted beam of radiation may then be analyzed to determine the presence of one or more interferents and/or certain physical dimensional characteristics of the sample container 20 or of the specimen 20A.

Sample quality station 30 may further comprise a conventional light (radiation) source 58 of non-collimated visible light (e.g., white light) that also directs a beam of light 58A onto the sample container 20. The light may be captured by a radiation capture device 62 such as a conventional digital camera digitizing means, or an array of photodetectors, after transmission through sample container 20. Reflectors and/or diffusers 60 may be provided to shape and obtain a uniform field of radiation. The radiation capture device 62 preferably has a digitizing means, which is also preferably monochromatic with at least eight bit high accuracy analog to digital capability. A digitizing means meeting these requirements is the model DT 3155 Frame Grabber, available from Data Translation. The digitized image may then be analyzed with a computer (e.g., a controller, processor, or microprocessor) containing an image processing software program to determine the presence of one or more interferents in the specimen 20A.

The scattering of coherent light by a small, single particle is equivalent to transforming the morphology of the particle into the angular distribution of scattered light. Mathematically, this transform is known as the Fourier transform. This is a well-known effect and, for some classes of particles such as spheres, the transform is known exactly. When a collimated beam of coherent light encounters a specimen of biological cells or structures, part of the light may be absorbed, part may be scattered, and the rest may be transmitted. Transmitted and scattered light may be measured in accordance with aspects of the invention to obtain certain information about the specimen 20A.

The scattering of coherent light by an ensemble of particles that are all within the coherence length of the light source is obtained by the superposition of the light scattered by individual particles. Thus, if the particles are uniform and dispersed randomly, the net scattering distribution is N times the scattering intensity of a single particle where N is the number of particles. This is also a well-known effect that has been used to both size and estimate a concentration of particles. These measurements may be made directly on the angular distribution of the scattered light or after performing a Fourier transform of the angular distribution. It has been discovered that particles such as fatty deposits of lipid present in the serum plasma portion 20SP have such an effect.

If the particles are not randomly dispersed, then the scattering from individual particles "interfere," creating a distribution of scattering intensity reflecting the organization of the individual particles. As a result, the tendency of particles to aggregate may be determined by measuring a fluctuation in intensity of the scattered light. If the particles are random, the "interferences" between the scattering from individual particles are also random, leading to a uniform and constant fluctuation at any angle. However, as particles begin to aggregate, the interference grows, leading to increased fluctuation that may be measured.

The specimen analysis process may start when a phlebotomist, physician, nurse, or health practitioner draws or collects a sample of blood from a patient and inserts the sample (specimen 20A) in a sample container 20. That sample container 20 (e.g., sample tube) of blood is sent to a hospital laboratory, blood diagnostic laboratory, or other location to be tested for health conditions such as: diseases, cancers, fertility, drugs of abuse, and other disorders. The specific test for a health condition(s) depends on the patient and there are hundreds of health conditions that may be assessed using blood diagnostic instruments and automated analytical testing systems in these laboratories and locations. Blood diagnostic instruments, or clinical analyzers, may analyze the blood samples and provide the analytical results identifying the presence or an amount of a component therein. Automated systems, such as described in FIG. 1A, are used to transport the samples to and from blood diagnostic analyzer instruments 32, 28, 42, as well as processing equipment such as centrifuge 24.

Hospital or blood diagnostic laboratories can typically handle thousands of patient specimens each day and are increasingly relying on instruments and automation systems to process these samples accurately and efficiently. However, the instruments can produce errors that result from defects in the quality of the sample of blood. Sample quality defects may include discoloration, unwanted particle presence, clotting, and/or insufficient sample volume inside the sample tube.

Most of these defects can be observed after the centrifugation process. The centrifugation process in centrifuge 24 may separate the red blood cells (e.g., the red blood cell portion 20RBC) from the serum or plasma portion 20SP, where the red blood cells are packed at the bottom of the sample container 20, and the serum or plasma portion 20SP (clear or relatively clear section) is at the top section of the sample container 20 (e.g., sample tube). The serum or plasma portion 20SP is where most of the defects such as discoloration, unwanted particle presence, and clotting may be observed.

In a non-automated lab, technicians visually and manually inspect the sample container 20 (e.g., sample tube) to determine whether a sample quality defect exists. In busy labs, that might not be done thoroughly or, due to the subjective nature of the inspection, the outcome may be highly variable. For example, there may be variations due to person-to-person inspection or even variations from one sample to the next sample when an individual person is inspecting.

In an automated lab, the samples are often automatically sent from the centrifuge to the analytical instruments (e.g., clinical analyzers), via an automation system, without the opportunity for inspection whatsoever. Many unwanted, problematic, and frustrating occurrences may be encountered when specimens 20A including these defects are provided to the one or more analytical instruments. For example, if the sample quality issue is discoloration or insufficient sample volume, the lab technician may have to remove the specimen 20A from the instrument and/or automation system and request a new sample of blood from that particular patient. This decreases efficiency in the lab and can be annoying to the patient because more blood has to be drawn from them, which may require additional visits to the phlebotomist.

In another example, if the sample quality issue is unwanted particle presence and/or clotting, the lab technician may have to perform additional pre-processing tasks for that sample before reinserting it into the system again for analysis. Additionally, the technician may have to stop the analytical instrument and/or automation system and clean certain equipment, such as probes and pipettes, on the system because of the particles that may have interfered with the assay (test).

Therefore, when any sample quality defect is encountered on an instrument, the assay results for that specimen may be erroneous and the efficiencies of the lab, such as test turnaround time or down time, may be negatively affected. The specimen 20A itself may also, in some instances, be wasted because the sample is analyzed before it has received the appropriate processing.

Lipemic Sample Detection

According to one broad aspect, the invention is directed at a method and apparatus (e.g., device) that may detect a lipemic specimen of a centrifuged sample container (e.g., sample tube) containing a specimen (e.g., blood) using a collimated light source, preferably a laser diode, and a radiation capture device (e.g., a digital camera) for enabling electronic image analysis and detection.

Lipemia is a specific sample quality discoloration defect, which may be resolved with special processing before the specimen 20A is tested or analyzed on an analytical instrument or placed on an automation system. The definition of lipemia (also spelled lipaemia) is the abnormally high presence of lipids (fats) in the blood. Lipids exist as small particles not soluble in water. Typically, the serum or plasma portion 20SP (FIG. 1B) is relatively clear. In a lipemic sample, however, the serum or plasma portion 20SP of centrifuged blood may appear to be white or milky in color due to the presence of the lipids. A common cause of lipemia is eating fatty foods. After the lab is aware the sample is lipemic, they may further process the specimen 20A to remove or reduce the lipids. For example, they may introduce a solvent or other material to reduce the amount of lipemia. Once this is complete, the specimen 20A can be properly analyzed by the clinical analyzer instrument (e.g., 32, 38, and 42) and the lab will be relatively more confident of the test results.

This aspect of the invention seeks to detect lipemia at the first possible instance (e.g., at the next processing station) after centrifugation of the specimen 20A. By detecting lipemia at that point in the process, the specimen 20A will not be wasted, erroneous test results will be prevented, and the patient test result delay will be minimized. When this sample quality station 30 is provided on a automated sample handling system 10, each specimen 20A will be screened for interfering levels of lipemia when it leaves the centrifuge 24 (See FIG. 1A). If an interfering level of lipemia is detected, the technician or user is alerted via a screen warning, warning bell, etc. The sample container 20 may then be routed to a place on the system 10 to wait for user corrective action or additional processing, such as to auxiliary processing station 30A. After the specimen 20A is corrected or additionally processed, it can be placed directly on an analytical instrument (e.g., 32, 38, and 42) for analysis, or back onto the track 14 of the automated sample handling system 10. In some embodiments, the automated sample handling system 10 might be able to perform this corrective action on a sample without user interaction. For example, the routing of the lipemic specimen would remove the specimen via robotic transport 30B and require additional processing at station 30A as a prerequisite to analysis on the analytical instruments 32, 38, and/or 42, for example.

In another aspect, the invention is directed at a method of determining a characteristic of a clinical analysis specimen contained within a sample container. In this aspect, the method comprises transmitting a beam of radiation through the clinical analysis specimen contained within the sample container; capturing the beam of radiation transmitted through the sample container; and analyzing the captured beam of radiation to determine a presence of one or more interferents within the clinical analysis specimen. For example, in one embodiment, the method is directed at determining a presence of lipemia in the serum or plasma portion 20SP of the specimen 20A. The presence of other interferents, such as hemolysis or icterus, may also be determined as discussed below.

Figure 1B:
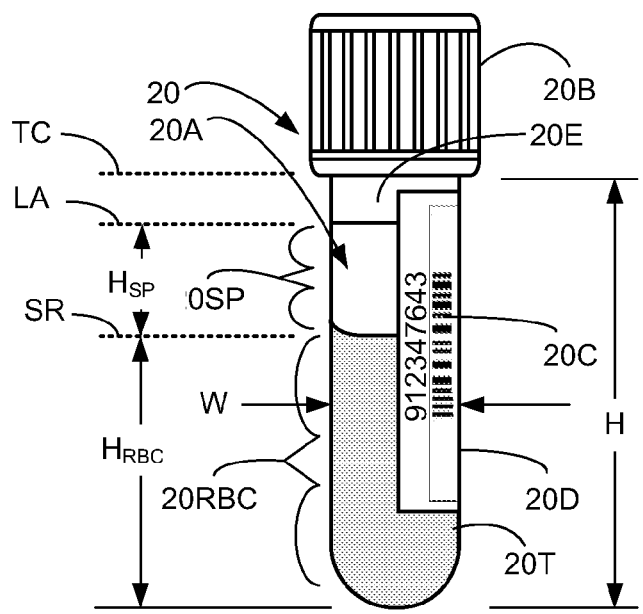
FIG. 1B is a side view of a labeled sample container including a centrifuged specimen, which may be analyzed for the presence of an interferent or a physical dimensional characteristic according to aspects of the present invention.
Figure 1C:
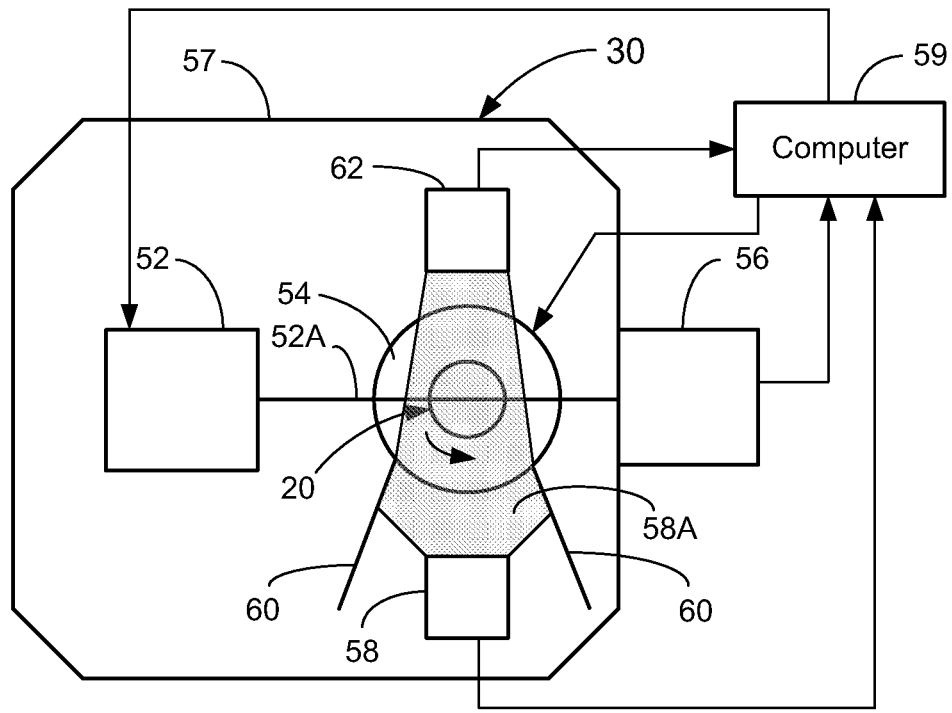
FIG. 1C is schematic top view of an embodiment of a sample quality station adapted to automatically analyze for the presence of an interferent or a physical dimensional characteristic before being automatically processed by one or more clinical analyzers of the automated sample handling system of FIG. 1A.
Figure 1D:
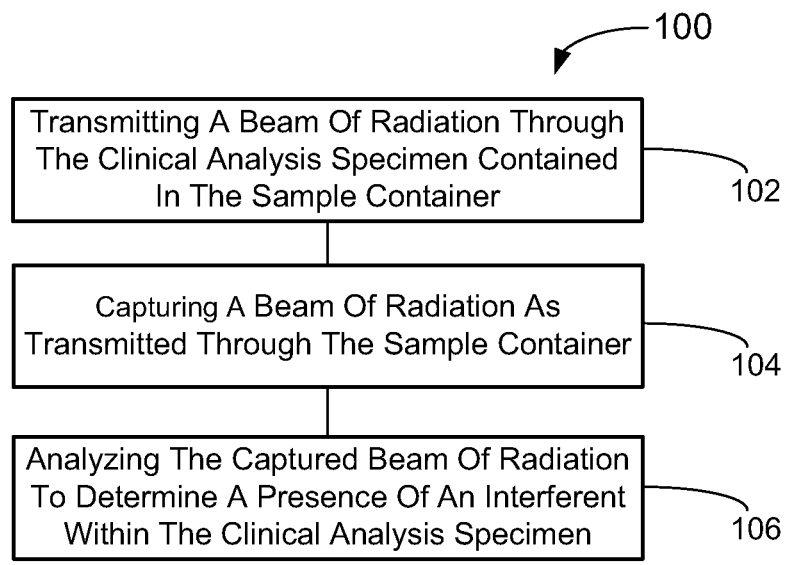
FIG. 1D is flowchart of a method adapted to automatically analyze for a presence of an interferent within a clinical analysis specimen.

According to the method 100, and referring to FIGS. 1B, 1C, and 1D, a step of transmitting a beam of radiation 52A through the clinical analysis specimen 20A contained in the sample container 20 (e.g., sample tube) in block 102 may be by using a radiation source 52, which may be a collimated light source, preferably generated by a laser diode, to project the beam 52A (e.g., a laser beam) onto a sample container 20 containing centrifuged blood having a red blood cell portion 20RBC and a serum or plasma portion 20SP. In the case where the radiation source 52 is a laser, the laser may be operated at any suitable wavelength and power. However, either 635 nm or 650 nm at 0.9 mWA are suitable. A radiation capture device 56, such as a digital camera, CCD, or other suitable digitizing device, may capture an image (e.g., a digital image) of the sample container 20 of blood along with an image of the beam of radiation 52A as transmitted onto or through the sample container 20 in block 104. A computer 59 containing a computer software program may be used for electronic image analysis of the digital image captured by the image capture device 56. The captured beam passing through the specimen 20A may be analyzed for the presence of an interferent within the clinical analysis specimen 20A in block 106. For example, the analysis may involve the detection of lipids as an interferent, for example. When the computer software successfully detects that a sample is lipemic, then that specimen 20A may not be immediately analyzed, and may be rerouted to another area on the instrument or automation system that is reserved for lipemic sample pre-processing activities (e.g., auxiliary processing 30C). The lab technician may then perform pre-processing activities and reinsert the specimen 20A on the analyzer instrument 32, 38, 42 or automated sample handling system 10.

The sample container 20 may be located inside a non-reflective box or enclosure 57 for optimal image capture. Also located inside the enclosure 57 may be the radiation source 52, as well as another light source 58 and diffusers 60 that may serve to properly illuminate the sample container 20 for additional quality image capture results (e.g., for a determination of hemolysis). The radiation capture device 56 (e.g., digital camera) may be located either inside of the enclosure 57 or outside of the enclosure 57 and receive the image through the aforementioned view window of the sample container 20. The sample container 20 may be positioned on a rotating holder 54, which may be controlled by a motor (e.g., a stepper motor not shown) to rotate the sample container 20 until a visible region (a window where a label 20D is not applied) of interest is displayed so that the radiation capture device 56 may capture the beam of radiation (possibly diffused or deflected) to determine a presence of an interferent within the clinical analysis specimen 20A. The captured radiation may be captured through the entire sample container 20 as in FIG. 10, or may be captured as a portion reflected from the sample or sample container as will be described with reference to FIG. 2A. A spot size of the captured image of the beam may be measured and correlated to a degree of lipemia present.

Specifically, lipids may interfere with spectrophotometric measurements of the analytical instruments mainly because they cause the light beam, used to measure absorbance in a sample within such instruments, to scatter. The scattered light is then not picked up by a radiation capture device of the spectrophotometer of the analytical instrument. Because the scattered light is not measured, it is assumed that the light was absorbed. Therefore, this will cause inaccurate analytical measurements.

Now referring to FIGS. 2A-2D another apparatus 200 and method 200A adapted to determine a presence of one or more interferents or physical dimensional characteristics of the clinical analysis specimen 20A or sample container 20 is illustrated. The apparatus 200 may be provided at the sample quality control station 30, for example. Like the previously-described embodiment, the apparatus 200 may include a rotating holder 254 adapted to rotate the sample container 20 so that the window may be oriented at a suitable position for image analysis in block 202A (see FIG. 2B). The method 200A and apparatus 200 may include a radiation source 252 that is adapted to transmit a beam of radiation 252A onto the clinical analysis specimen 20A contained in the sample container 20 (e.g., sample tube) in block 204A. The beam of radiation 252A may be coherent. Additionally, the beam of radiation 252A may be collimated. In the depicted embodiment, the beam of radiation 252A may be projected onto the sample container 20 in the form of a laser line (shown dotted), which may be formed by optical line generator 252B coupled to the radiation source 252. A radiation capture device 256 may be adapted to capture an image of a beam as reflected from the sample container 20 or specimen 20A in block 206A. Finally, in block 208A, the captured image of a beam and sample container 20 may be analyzed by a computer 259 to determine a presence of an interferent within the clinical analysis specimen 20A. The analysis may include blob analysis wherein the various line segments of the reflected image are grouped and analyzed as blobs and characterized in terms of their height, width, and relative location in the captured image. These parameters may then be compared to values in a look up table, for example. From this, a lipemic index value may be determined. Moreover, certain physical dimensional and other parameters of the specimen 20A or sample container 20 may be determined (e.g., height of the sample container tube 20T (to the tube/cap interface TC), overall fill height, vertical height of the serum or plasma portion 20SP, vertical height of the red blood cell portion 20RBC, etc.). Additional interferents may be determined using a radiation source 258 (e.g., a white light source). The radiation source 258 may be substantially vertically aligned with radiation source 252.

As in the previous embodiment, a holder 254 is adapted to receive and hold the sample container 20 in a generally upright orientation. The holder 254 may be coupled to, and rotated by, a motor 255 (e.g., a stepper motor) to rotate the label 20D such that the window is appropriately positioned as shown in FIG. 2B to allow the beam 252A to be projected onto the sample container 20 through the window. Once the sample container 20 and label 20D are properly rotationally positioned to expose the window, the beam 252A may be projected onto the sample container 20 and the image recorded. As a result, several possible outcomes may be achieved based upon reflections from the back wall 257A of the enclosure 257, and reflections from the front and rear walls of the sample container 20. The results depend upon the condition of the specimen 20A in the sample container 20.

Figure 3:
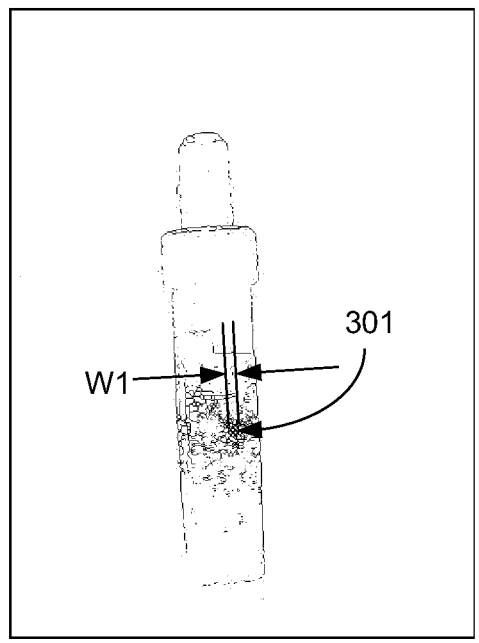
FIG. 3 is a representative illustration of light reflection from a sample container containing a normal specimen.
Figure 4:
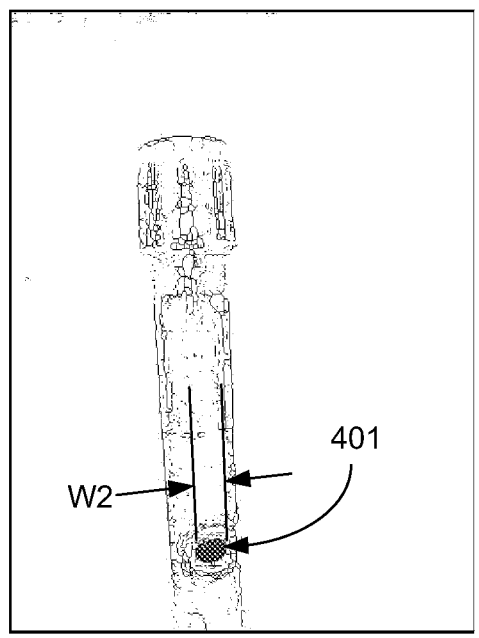
FIG. 4 is a representative illustration of light reflection from a sample container having a specimen with an elevated amount of lipemia, i.e., a lipemic specimen.
Figure 5D:
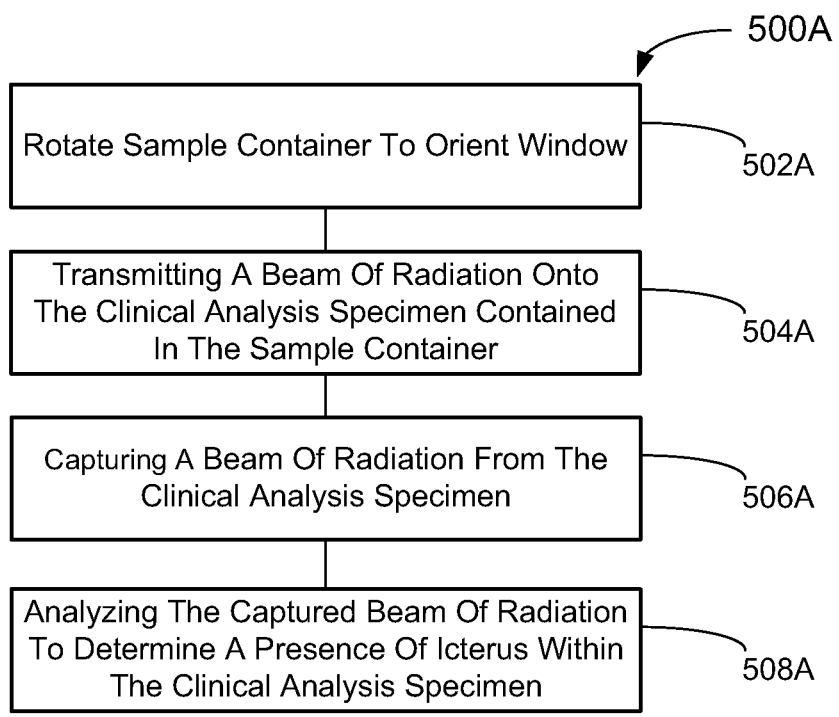
FIG. 5D is a flowchart illustrating a method of detecting icterus according to an aspect of the present invention.
Figure 6:
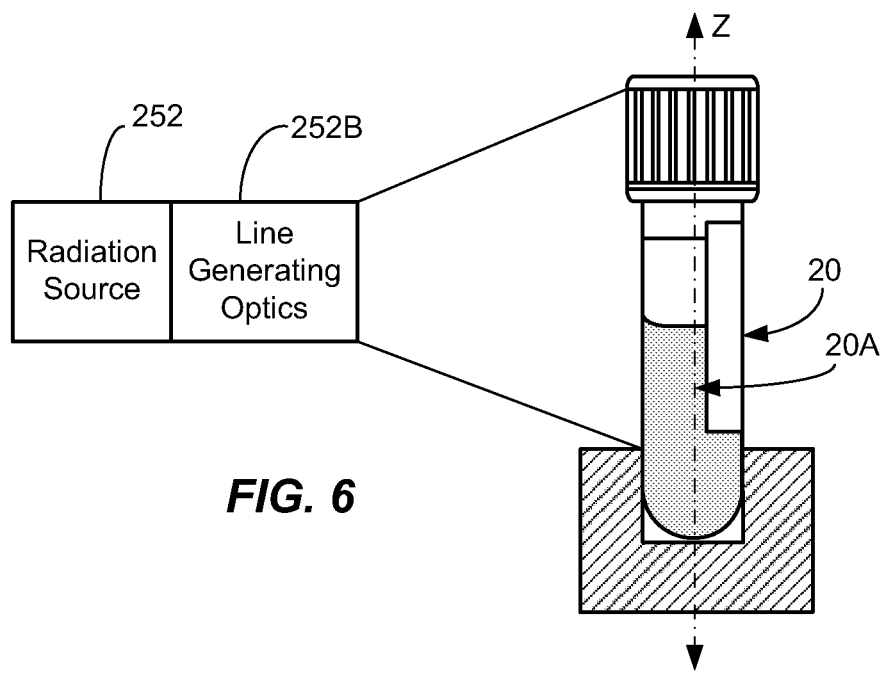
FIG. 6 is a side view illustration of an apparatus adapted to provide a vertically-oriented laser line from a radiation source (e.g., laser) along a longitudinal Z axis of the sample container.

In a lipemic sample, the property of light scattering that was described to cause problems for spectrophotometry during analysis is the very property that will be taken advantage of for measuring a lipid interferent. It was observed by the inventor that, when a beam 52A, 252A of radiation from a radiation source 52, 252 (e.g., laser) passes through the serum or plasma portion 20SP of a normal specimen 20A, there is some light reflection from both the front and back surfaces of the sample container 20, and some minor reflection from the specimen 20A itself, as is shown in FIG. 3. On a sample with high concentration (i.e., which are lipemic), there is some light reflection from the front surface but, as the laser beam 52A, 252A enters the sample (specimen), there is immediate dispersion (scattering) and light reflecting from the specimen 20A, as shown in FIG. 4. These same pictures with some simple image processing may further highlight the distinctive difference a lipemic sample has when exposed to a radiation source 52, 252 (e.g., a laser). Further vision analysis and use of line generating optics to project a beam line (e.g., a laser line beam) onto the sample container 20 and specimen 20A may provide improved detection by allowing detection of the interfaces between air and serum or plasma portion 20SP in the container 20, as well as an interface SR between the serum or plasma portion 20SP and the red blood cell portion 20RBC. Additionally, an interface TC between the sample tube 20T and cap 20B of the container 20 may be determined.

According to this embodiment of the invention, the method 100 may include providing a radiation source 52 (252) that may transmit a beam of radiation onto the sample container 20 containing the specimen 20A in block 102, and then in block 104, a radiation capture device 56 (256) may capture an image of the sample container 20 with beam 52A (252A) including reflections and/or dispersions superimposed thereon in block 106. The image may contain a laser beam spot 301, 401 as shown in FIGS. 3 and 4. FIG. 3 illustrates a normal spot size 301 and FIG. 4 illustrates an image of a lipemic sample including a relatively enlarged spot size 401. For example, the spot 401 may be enlarged having a width dimension W2, as compared to a normal sample having a spot 301 with a smaller width dimension W1. Processing software may measure a size of the spot 301, 401 and correlate that spot size to a degree of dispersion caused by the specimen 20A as the beam 52A (252A) disperses within the specimen 20A. This, in turn, suggests a lipid concentration. Generally, the only substances that cause such dispersion in a specimen 20A are lipids but, regardless of the substance, if the light going through the specimen 20A is appreciably dispersed, an analytical measurement error is likely, and the lab should be appropriately informed, such as by generating a screen warning, sounding an alarm, unloading the lipemic specimen 20A, or stopping the automated system 10. As discussed above, the relative amount of dispersion, which may be dictated by the spot size (e.g., a spot width) may be correlated to a lipemic index. If the lipemic index exceeds a preset threshold, the specimen 20A may be determined to be lipemic. In the case where line generating optics are used, the captured image (e.g., reflected image) may also be used to determine the presence of one or more interferents by examining the portions of the image. Optionally or additionally, since the presence of lipemia is generally indicated by a white color, the serum or plasma portion 20SP may be further analyzed using the radiation source 58 and capture device 62 to generate an image thereof. RGB values (a red, green, blue system of color analysis) obtained from the captured image may be analyzed by comparing them to stored threshold values (indicative of a certain hue of white) to indicate the presence of lipemia.

At least five things make the lipemia measurement technique relatively cost effective. One is that the pre-screen consumes none of the specimen 20A; it does not require an open sample container 20 or need to come in contact with the specimen 20A in any way. Two is that it is fast; the image acquisition and analysis may be significantly faster than chemistry analysis techniques. Three is that there is no variable cost; with no consumables, the cost per sample analyzed is substantially zero. Four is that the pre-screen may be performed early in the pre-analytical processing phase of specimen preparation; any necessary corrective action may be undertaken on the specimen 20A before clinical analysis is attempted. Five is that the pre-screen may measure directly, without any chemical analysis, the phenomenon dispersion that may cause interference in the spectrophotometer.

Additionally, the capture image may be used to identify such items as: 1) the vertical interface location TC between the sample tube 20T and sample cap 20B, which may establish a relative height (H) of the sample container 20 being used; 2) the vertical interface location SR between the serum or plasma portion 20SP and the red blood cell portion 20RBC; and 3) the vertical interface location LA between the serum or plasma portion 20SP and the air 20E in the sample container 20.

As shown in FIG. 2B, it can be seen that the radiation source 252 may be angularly offset from the capture device 256 such that an offset angle o of between about 10 and 45 degrees, and preferably about 22 degrees, is provided between a vector 252V of the light beam 252A and a vector 256V of the capture device 256 that is aligned between the center of the capture device and a center of the sample container 20. As the beam 252A is projected onto the sample container 20, in a first case, the beam 252A may encounter the sample tube containing air, such as when the beam (or portion thereof) is aligned vertically with the air in the sample tube 20T. In this case, the beam will pass entirely through the sample container and be projected onto the back wall 257A of the enclosure 257. The position of beam of radiation 252A as it is projected onto the back wall 257A will then be captured by the capture device 256, as indicated by reflected beam 252C. Accordingly, the image of the captured beam and the position thereof in pixel space (both vertically and horizontally) may be used to determine certain physical dimensional characteristics of the clinical analysis specimen 20A and/or of the sample container 20.

For example, as shown in FIG. 2E, if the reflected beam 252C (see also FIG. 2B) is determined to be positioned at a certain location (e.g., outside of the physical perimeter of the sample tube 20T) on the image, then this may be indicative of air 20E being present in the sample tube 20T. Also shown in FIG. 2E is a beam reflection 252D that may be indicative of the presence of a cap 20B. Because the reflection is from near the front of the sample container 20, the reflection of the beam 252A appears on the relative left side of the image as captured reflected beam 252D (see FIG. 2B). That horizontal location to the relative left side in conjunction with its relatively high location in the image is indicative of a cap 20B. This may be used to determine the tube/cap interface TC and, thus, a height of the sample container 20. An overall width of the container 20 may also be obtained from the image. Accordingly, a size of the sample container may be classified. Of course, the relative location of these reflected beams in the image depends on the angular offset ø of the radiation source 252 and the spacing of the back wall 257A relative to the holder 254.

Figure 2A:
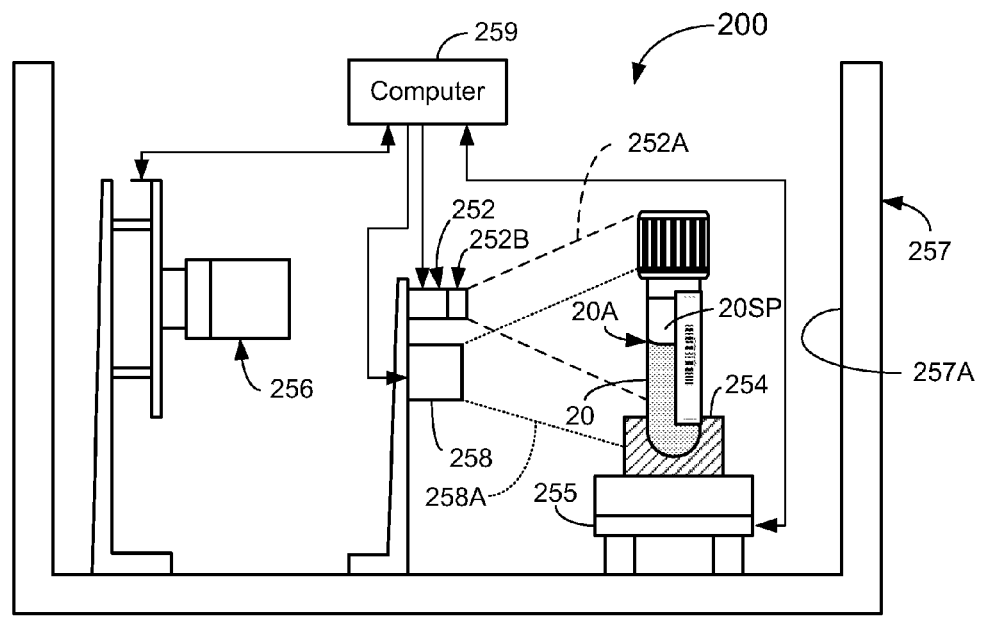
FIG. 2A is schematic side view of another embodiment of a sample quality station adapted to analyze for a presence of an interferent or a physical dimensional characteristic of the clinical analysis specimen or sample container.
Figure 2B:
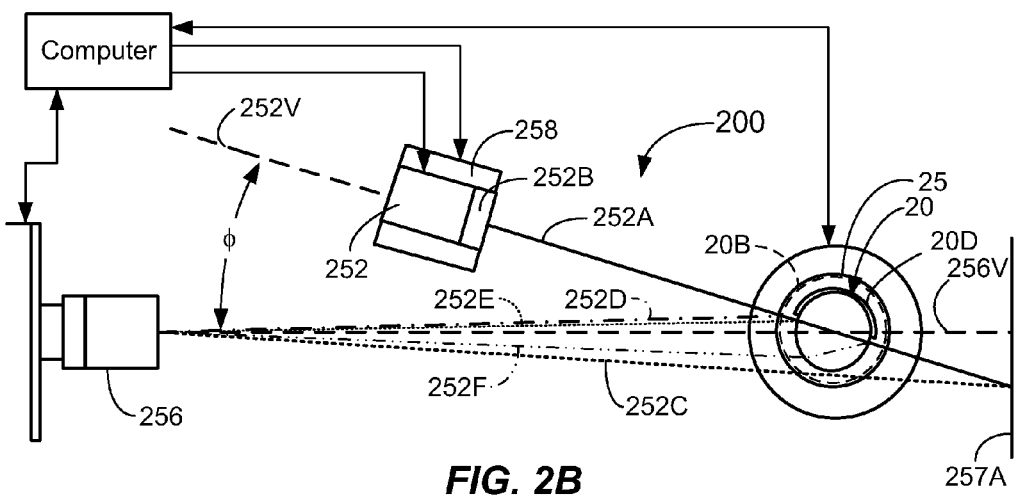
FIG. 2B is schematic top view of a portion of the sample quality station of FIG. 2A.
Figure 2C:
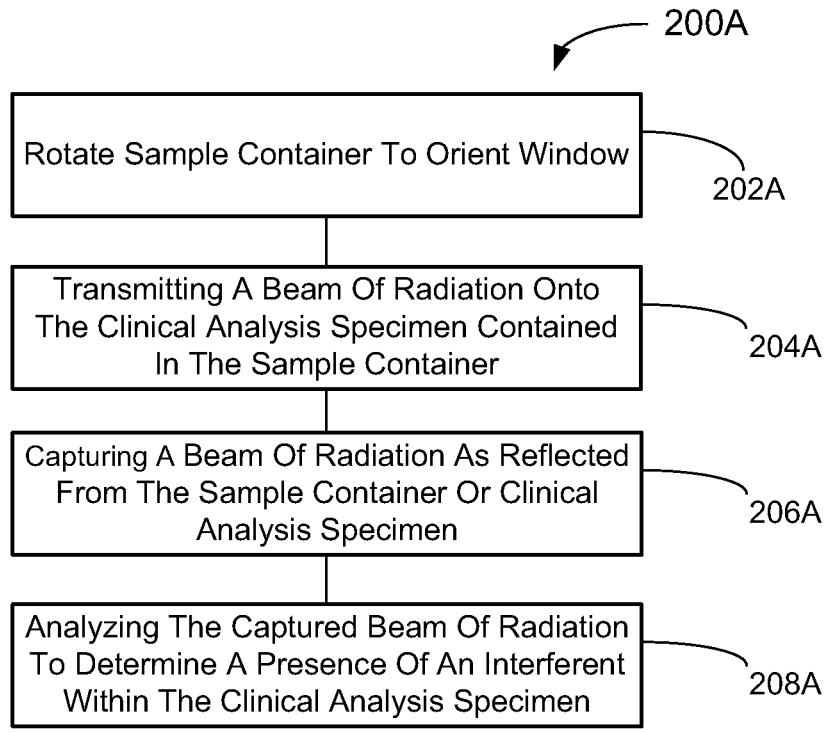
FIGS. 2C-2D are flowcharts illustrating methods according to aspects of the present invention.

As shown in FIG. 2F, an image of a label 20D is shown when the sample container 20 is rotated so that the label 20D is directly oriented/aligned with the capture device 256. The processing software may be used in conjunction with the motor 255 (and rotational position sensors thereof) to determine when this "label pattern" appears as a function of rotation of the sample container 20 to determine the rotational location of the window, for example. Once the window is determined, the sample container 20 may be oriented as shown in FIG. 2B, for example, for carrying out the quality control imaging. If radiation sources 252, 258 are vertically aligned (as in the FIG. 2A-2B embodiment) then no further rotation may be needed for the analysis/detection of hemolysis or icterus.

FIG. 2G illustrates a sample container 20 including a specimen 20A with a serum or plasma portion and red blood cell portion 20RBC. As the beam 252A is projected onto the sample container 20 and specimen 20A contained therein, certain image patterns are evident based upon the condition of the specimen 20A. For example, the reflection pattern of the red blood portion 20RBC may appear as a reflection similar to that of the label (albeit slightly offset therefrom and possibly slightly wider in width). However, in a lipemic specimen, the image will be relatively wider, depending upon the degree of lipemia present. The wider the image, the relatively higher amounts of lipemia that are indicated. The relative width measure W and vertical location of the image may be measured by the image processing software. This width measure W, which is dependent on the reflection and dispersion of the light beam 252A from and in the specimen 20A, may be correlated to a degree of lipemia present in the serum or plasma portion 20SP of the specimen 20A. The captured beam is shown between lines 252E and 252F in FIG. 2B. Again, the location of these is indicative of the amount of reflection and dispersion of the light beam 252A in the specimen 20A.

It also should be apparent that, from the captured images of the beam in FIG. 2G, additional information concerning the physical dimensional characteristics of the specimen may be determined as will be described more fully below.

As shown in FIGS. 2H and 2I, negative images of reflections from an actual normal specimen 20AN (e.g., normal sample in FIG. 2H), an abnormal specimen 20AA (e.g., abnormal Lipemic sample in FIG. 2I) and sample container 20A are shown. As can been seen, each image includes:

a tube cap interface TC, location of the upper end of the label LE, a liquid-air interface LA (interface between the air in the sample tube 20T and the serum or plasma portions 20ANSP, 20AASP, the serum-separator interface SS, which is the interface between the serum or plasma portions 20ANSP, 20AASP of the specimen 20AN, and the serum separator portions 20ANSS, 20AASS, and the separator-red blood cell portion interface SSR, which is the interface between the serum separator portions 20ANSS, 20AASS of the specimens 20AN, 20AA, and the red blood portions 20ANRBS, 20AARBS.

Many times specimens 20A may include a serum separator gel that is added to aid in the separation of the serum or plasma portion 20SP from the red blood cell portion 20RBC. The method and system of the invention may readily determine these additional interfaces SS and SSR, as well as the label end LE.

Hemolyzed Specimen Detection

According to another broad aspect, the invention is directed at a method and apparatus (e.g., device) that may be used to detect a hemolyzed sample (specimen) contained in a sample container 20 of centrifuged blood. The method 500 as shown in FIG. 5C utilizes a radiation source for projecting light radiation (e.g., a white light) onto the sample container 20, a radiation capture device (e.g., a digital camera) for electronic image capture, and then analysis of the captured image to detect hemolysis.

Hemolysis is a sample quality discoloration issue, and it cannot be resolved with special processing. Hemolysis (also spelled haemolysis) may occur when the red blood cells rupture and the hemoglobin inside is released into the serum/plasma section 20SP (FIG. 1B) of the centrifuged blood specimen 20A, thus giving the serum or plasma section 20SP a more reddish color or appearance. Along with a more reddish color, potassium may be released into the serum or plasma portion 20SP, which may give erroneous results when tested on an analytical instrument. Incorrect blood collection, handling, storage, and/or processing may cause hemolysis.

In the case of a clinical analysis specimen 20A suffering from hemolysis, the usual procedure is to redraw another specimen 20A from the patient to ensure that a good quality specimen 20A is presented to the analytical instrument(s). Once the new specimen 20A is processed, it may be successfully analyzed without the interfering hemoglobin.

In another aspect, the invention can detect the presence of hemolysis in the specimen 20A, thereby saving the analytical instrument(s) from performing analytical testing on a specimen 20A whose results may be suspect. When the specimen 20A is imaged and analyzed for lipemia, the serum or plasma portion 20SP is visible through the side (window) of the sample container 20 (e.g., test tube). At this time, at the quality control station 30, there is an opportunity to record and analyze the color of the serum or plasma portion 20SP in order to make a basic assessment for hemolysis. This assessment may be solely performed or may be performed in conjunction with the lipemic analysis at the quality control station 30.

In the assessment for hemolysis, the radiation source 52 (e.g., collimated light source or laser) would be turned off. As described above, the "window," or region of interest, where there is no label 20D may have already been found via rotation of the sample container 20 during the earlier search, such as when analyzing for potential lipemia. If not, the procedure above may be employed wherein in block 502 the sample container 20 is rotated to orient the window relative to a radiation source and appropriately position the sample container 20 for hemolysis assessment. Additionally, with image capture and processing for hemolysis analysis, the area under consideration is reduced to just the serum or plasma portion 20SP in the "window."

Unlike a lipemic specimen, when the computer software successfully detects that a specimen 20A is hemolyzed, then that specimen 20A may continue to be tested and analyzed on the clinical analytical instrument(s) without delay. After completion of the analytical testing, the specimen 20A may be rerouted to an area on the instrument or the automated sample handling system 10 that is reserved for evaluating hemolyzed samples. For any successful detection of a hemolyzed sample, the computer may provide an alert that will be displayed on a display (e.g., computer screen) at the quality control station 30, on the analytical instrument, or automated sample handling system 10 to alert personnel (e.g., technician) for further evaluation and/or decision making.

To improve an ability to convey the assessment of a hemolyzed sample to laboratory personnel, an image of the sample container 20 (e.g., test tube) including the specimen 20A determined to be hemolyzed may be displayed. This may be displayed along with collaborative information such as, but not limited to, reference images of various hemolyzed specimens, color spectra for comparison, sample's assessed position in color spectra, and/or text description of issue and/or suggested laboratory action to take.

In addition, in some embodiments, if a hemolyzed specimen 20A were detected on a sample quality station 30 of an automated sample handling system 10, the specimen 20A may be sent on to an analytical instrument (e.g., a specialized clinical analyzer) where a precise level of hemolysis can be measured and characterized. Analytical instruments are much better at determining levels of hemolysis and often have rules that determine the exact concentrations of hemoglobin that affect assay results for the various assays ordered for the specimen. As a result, some test results can be reported before the specimen redraw and retesting occurs. However, it should be apparent that, with the early detection of hemolysis, the laboratory technician can decide on the urgency of a redraw with the confidence that the automated sample handling system 10 may be able to report the results, even though the specimen 20A may contain some level of hemolysis. Additionally, or optionally, an alert could also be used to identify which ordered assay results are likely to have an adverse effect by the extent of hemolysis that has been detected. With this enhanced presentation, the task of making the correct clinical decision may be made significantly easier and less prone to error.

The action to take when a sample is hemolyzed is based on rules defined by the laboratory to align with their specific procedures. The hemolysis threshold that triggers the rules may also be established by the laboratory, and may vary from test to test, which may also be subsequently undergone. The lab would use the quality control specimen (e.g., a reference sample 20R—see FIG. 5A) to establish a threshold hemolysis level that triggers the alert. For example, sample 20R shown in FIG. 5A illustrates a reference sample having a serum or plasma portion 20SP with an elevated level of hemolysis. Sample 20H in FIG. 5B illustrates a sample with an elevated level of hemolysis above the threshold. An example of various levels of hemolysis may be seen in an article in Clinical Chemistry (Vol. 24, No. 11, 1978) entitled "Effect of In Vitro Hemolysis on Chemical Values for Serum" by Joseph J. Frank, Edward W. Bermes, Margaret J. Bickel, and Bruce F. Watkins.

Now referring to FIGS. 1C and 5C, in order to determine an amount of hemolysis present in the specimen 20R (FIG. 5A) contained in the sample container 20, a radiation source 58 may project a light beam 58A onto the sample container 20 in block 504, and an image may be captured by the radiation capture device 62 in block 506. This image may be analyzed in block 508 to determine a color of the serum or plasma portion 20SP. A red, green, blue (RGB) system of color analysis may be employed. Accordingly, the light capture device 62 may be any suitable camera or digitizing array capable of discerning RGB hues. The respective red (R) hue may be measured on a scale from 1 to a maximum number (e.g., 1-256). Any specimen 20A, which may include a red hue above a threshold value as established by calibrating with the reference sample 20R, may be determined to be a hemolyzed sample. Optionally, more than one color may be measured and thresholds may be set based upon more than one detected color. Image analysis in block 508 may include measuring the color of the serum or plasma portion 20SP in an area located vertically between the liquid-air interface LA and the interface SR, and roughly centered on the window. Based upon the detected hue or hues, a hemolytic index may be determined and reported, or otherwise conveyed from the quality control station 30. The hemolytic index may be roughly determined based upon correlated ranges of the measured hue values as shown in Table 1 below, for example.

TABLE 1

| Hemolytic Index | | | | |
|---|---|---|---|---|
| Hemolytic Index Value | 1 | 2 | 3 | 4 |
| Red Hue Range | 0-64 | 65-128 | 129-192 | 193-256 |

The above method 500 for determining a hemolysis interferent may be also accomplished using the apparatus shown in FIG. 2A. The additional white light radiation source 258 may perform the illumination function and the radiation capture device 256 may capture the image thereof. Analysis for hemolysis may be as above described.

The hemolysis measurement technique shares most of the advantages indicated above for the lipemic detection. One advantage is that the hemolysis pre-screen consumes no specimen 20A; it does not require an open sample container 20 or need to come in contact with the specimen 20A in any way. Two is that it is relatively fast; the image acquisition and analysis may be significantly faster than chemistry analysis techniques. Three is that there may be substantially no variable cost; with no consumables, the cost per specimen analyzed is substantially zero. Four is that the hemolysis pre-screen may be performed early in the pre-analytical processing phase of specimen preparation; hospital personnel can be alerted as early as possible that there is a condition of the specimen 20A that may require their attention.

Icterus Detection

According to another broad aspect, the invention is directed at a method and apparatus (e.g., device) that may be used to detect icterus in a specimen 20A contained in a sample container 20 of centrifuged blood. An icterus interferent may arise, for example, from an excess of bilirubin, the result of decaying red blood cells being converted in the spleen into bilirubin. Levels of bilirubin above 2-3 mg/dl are generally visibly yellowish/brownish in color and may, in particular, adversely affect enzyme-based immunoassays. Such a condition is also termed bilirubinaemia.

The icterus detection method 500A (see FIG. 5D) is similar to that for detecting hemolysis. The method 500A may first rotate the sample container to orient the window in block 502A. Next, the method 500A may utilize a radiation source (e.g., radiation source 58, 258) for projecting or transmitting a beam of light radiation 58A, 258A (e.g., white light) onto the sample container 20 containing a clinical analysis specimen 20A in block 504A. The apparatus may be as shown in FIG. 10 or FIG. 2A-2B, for example. A radiation capture device (e.g., 56, 256 such as a digital camera) adapted for digital electronic image capture may capture an image from the clinical analysis specimen 20A of the beam 52A, 252A as reflected from or passing through the sample container 20 and serum or plasma portion 20SP of the specimen 20A in block 506A. A computer 59, 259 may then perform an analysis of the captured image for the presence of icterus. According to the method, the same digital image that was taken for the hemolysis detection may optionally be used for icterus detection. In this case, the image may be analyzed for the presence of a yellow and/or brown color. Again this may be accomplished via measuring with the radiation capture device 56, 256 (e.g., a digital camera having RGB capability or an RGB sensor) a degree of yellow and/or brown present in the serum or plasma portion 20SP of the specimen 20A. Optionally, a sensor using the CMYK system may be employed. Range values for each of yellow and/or brown may be experimentally determined and set and may be used to provide an icteric index. For example, a range from 1 to 4 may be employed. Other suitable icteric index values may be used. A central portion of the serum or plasma portion 20SP for analysis may be located via the image analysis technique described herein for determining the location of interfaces LA and SR.

Physical Dimensional Characteristics Detection

Figure 2D:
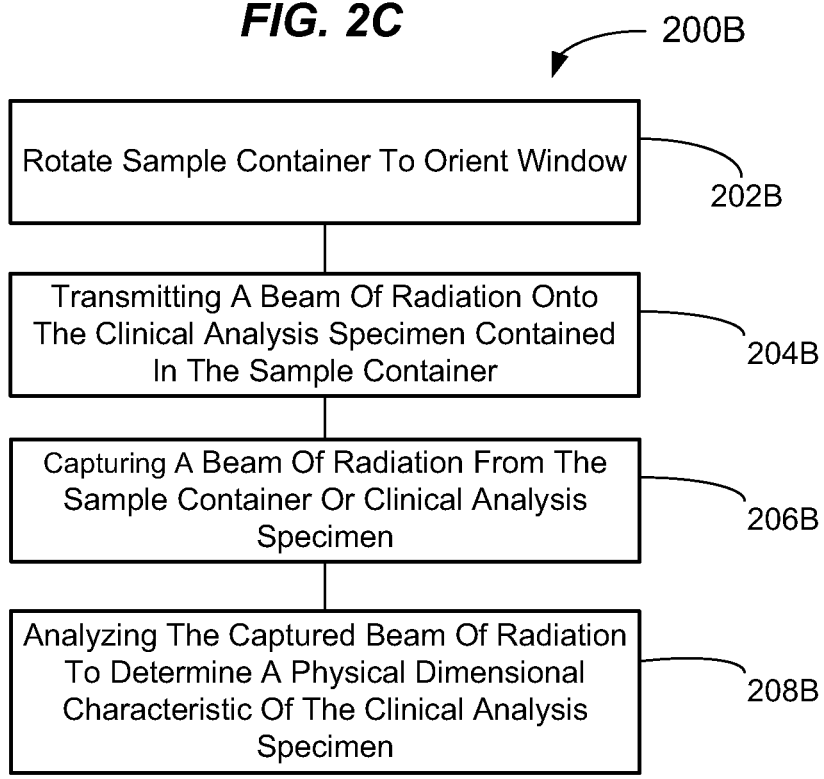

According to another broad aspect, the invention is directed at a method and apparatus (e.g., device) that may be used to detect a physical dimensional characteristic of a specimen 20A contained in a sample container 20 of centrifuged blood. The method 200B as shown in FIG. 2D first rotates the sample container 20 to orient the window in block 202B, as described above. Next, a radiation source 252 transmits (projects) a beam of light radiation (e.g., a laser) onto the specimen 20A in sample container 20 in block 204B. A radiation capture device 256 (e.g., a digital camera, CCD, or the like) may capture a digital electronic image of the beam from the specimen (as either reflected or passing through the specimen 20A) in block 206B. Finally, in block 208B, a computer 259 may then perform an analysis of the captured image to detect a physical dimensional characteristic of a specimen 20A. The physical dimensional characteristic may include at least one of: 1) the vertical interface location SR between the serum or plasma portion 20SP and the red blood cell portion 20RBC; and 2) the vertical interface location LA between the serum or plasma portion 20SP and the air 20E in the sample container 20.

Fill Volume Detection

According to yet another broad aspect, the invention is directed at a method and apparatus (e.g., device) that may detect a total volume of a centrifuged or un-centrifuged specimen 20A in a sample container 20 (e.g., tubes of blood). The method and apparatus may employ a radiation source 52, 252 (e.g., a collimated light source, preferably a laser diode), a capture device 56, 256 (e.g., a digital camera) for image capture, and a computer 59, 259 for executing a program for electronic image analysis and detection. The method may determine a location of the liquid-air interface LA as discussed above. The fill volume of the specimen 20A in the sample container 20 may be mathematically estimated based upon the location of the interface LA and the overall width of the particular sample tube 20T.

Hematocrit Level Detection

According to another aspect of the invention, certain physical dimensional characteristics of the specimen 20A may be determined. For example, in another broad aspect, the invention is directed at a method and apparatus (e.g., device) that may detect a hematocrit level of a specimen 20A (e.g., a centrifuged tube of blood). The method may use a collimated light source, preferably a laser diode, and a digital camera for electronic image analysis and detection. The hematocrit level may be determined by the method described above by identifying via image analysis, a location of the interface SR between the serum plasma portion 20SP and the red blood cell portion 20RBC, or the interface SSR when a serum separator is utilized. The packed red blood cells at the bottom of the sample tube 20T have yet a different light pattern when exposed to the radiation source (e.g., laser). From the captured image, a vertical location in the image of the interface SR of the red blood cell portion 20RBC for the specimen 20A may be determined. Accordingly, a relative height or volume of the red blood cell portion 20RBC may be determined.

Plasma or Serum (Supernatant) Level Detection

According to yet another broad aspect, the invention is directed at a method and apparatus (e.g., device) that may detect a plasma or serum (supernatant) level of a specimen 20A of centrifuged blood contained in a sample container 20. The method can detect the different light patterns between the serum or plasma portion 20SP and the air 20E above it, as well as the hematocrit level or serum separator level below it. The method may readily be used for specimens 20A where the serum or plasma portion 20SP is a "clear" or normal specimen, but may also, in most cases, detect the hematocrit level even in a highly lipemic sample. The method may use a radiation source (e.g., a collimated light such as 52, 252), preferably a laser diode, and a digital camera or the like as the capture device 56, 256, and a computer 59, 259 for electronic image analysis and detection. The method described above may be used for detecting the liquid-air interface LA as well as the interface SR or interface SSR. Additionally, the SR value (or SSR value) and the LA value may be used to determine a relative ratio between the red blood cell portion 20RBC and the serum or plasma portion 20SP. Of course, the overall height of the specimen 20A may be determined by the vertical location of interface LA in the image. Likewise, a respective height of the red blood cell portion 20RBC and the serum or plasma portion 20SP may be determined.

Sample Container Physical Characteristic Detection

In another aspect of the invention, certain physical dimensional characteristics of the sample container 20 may be determined. For example, a height or width of the sample tube 20T may be determined. Thus, according to yet another broad aspect, the invention is directed at a method and apparatus (e.g., device) that may detect a physical dimensional characteristic of a sample container 20 (e.g., sample tube) using radiation source 52, 252 (e.g., a collimated light source, preferably a laser diode), a capture device 56, 256 (e.g., a digital camera) for image capture, and a computer 59, 259 for executing a program for electronic image analysis and detection. The method may determine a location of the tube-cap interface TC as discussed above and use that information to determine a size of the sample container 20. Further image analysis may be utilized to determine a width of the sample tube 20T at the location of the serum plasma portion 20SP.

Specimen Separation Detection

According to yet another broad aspect, the invention is directed at a method and apparatus (e.g., device) that may detect whether a specimen 20A has been processed in a centrifuge to achieve separation (or not). The method may detect different light patterns between the serum or plasma portion 20SP described according to method and the red blood cell portion 20RBC. As a result it can be concluded that a specimen 20A has undergone separation if a serum or plasma level 20SP can be measured. For the converse conclusion, that a specimen 20A has not undergone separation, the whole blood in the sample container 20 will have a different light pattern when exposed to the radiation source 52, 252 (e.g., a laser).

Alternatives

Figure 7:
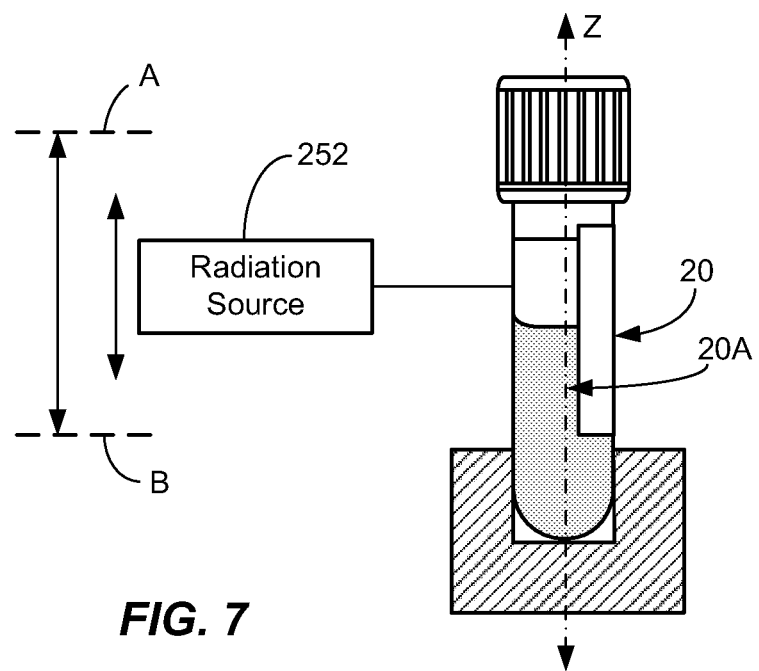
FIG. 7 is a side view illustration of an apparatus adapted to sweep a beam (spot) from a radiation source (e.g., laser) along a longitudinal Z axis of a sample container.

There are several alternative embodiments of this invention. In one embodiment shown in FIG. 6 and described above with reference to FIGS. 2A and 2B, line generating optics 252B are coupled to a radiation source 252 (e.g., a collimated source such as a laser) to project a laser beam 252A in the form of a "line" onto the sample container 20 and specimen 20A. In another embodiment as shown in FIG. 7, the radiation source 252 may be moved vertically along a vertical axis aligned with the Z axis and simply sweep a spot of the laser beam longitudinally along the sample container 20 and specimen 20A between limits A, B. In this embodiment, the width, vertical location, and horizontal location of the spot at various vertical positions may be measured by a rotationally offset capture device 256 as described above. This data may be correlated to be able to locate the tube-cap interface TC, liquid-air interface LA, the SR interface, the SS interface, the SSR interface, as well as the presence of lipemia.

While the quality control station 30 may be ideally located such that the pre-screening is performed immediately after centrifugation as a process screen, it may be advantageous to include this feature directly on a clinical instrument or clinical analyzer. For example, stand-alone clinical instruments and analyzers that are not connected to an automation system could use this technique to validate specimens prior to clinical analysis. If a specimen exceeds a predefined level of lipemia, hemolysis, supernat level, fill volume, etc. that is incompatible to the analytical instrument, the user could be notified to take corrective action. In some cases, the corrective action may be automated on the instrument (i.e., dilution as a remedy). Optionally, in some embodiments the analytical instrument may also simply use the measurement of lipemia in the specimen to correct the spectrophotometer readings to account for the scattered light not reaching its detector of the clinical instrument.

It should be readily appreciated by those persons skilled in the art that the present invention is susceptible of broad utility and application. Many embodiments and adaptations of the present invention other than those herein described, as well as many variations, modifications, and equivalent arrangements, will be apparent from, or reasonably suggested by, the present invention and the foregoing description thereof, without departing from the substance or scope of the present invention. Accordingly, while the present invention has been described herein in detail in relation to specific embodiments, it is to be understood that this disclosure is only illustrative and exemplary of the present invention and is made merely for purposes of providing a full and enabling disclosure of the invention. This disclosure is not intended to limit the invention to the particular systems, apparatus, or methods disclosed, but, to the contrary, the intention is to cover all modifications, equivalents, and alternatives falling within the spirit and scope of the invention.

What is claimed is:

1. A method of determining a characteristic of a clinical analysis specimen contained within a sample container, comprising:

orienting the sample container until a view window in the sample container is displayed, wherein the sample container is in an upright position and has a label provided thereon, the view window provided where the label is not located;

transmitting a first beam of radiation from a first radiation source comprising a collimated light source, and a second beam of radiation from a second radiation source comprising a white light source through the clinical analysis specimen contained within the sample container wherein the first beam and the second beam are transmitted onto a first side and a second side of the sample container, respectively, the second beam nonparallel with the first beam;

capturing first captured beam and the second captured beam of radiation transmitted through the clinical analysis specimen contained in the sample container via a first radiation capture device and a second radiation capture device wherein the first radiation capture device and the second radiation capture device are located on sides of the sample container opposite the first side and the second side, respectively; and analyzing the first captured beam of radiation to determine a physical dimensional characteristic of the sample container or a physical dimensional characteristic of the clinical analysis specimen, and analyzing a second captured beam of radiation to determine a presence of one or more interferents in an endogenous state within the clinical analysis specimen.

2. The method of claim 1, wherein the first beam of radiation has a property selected from a group consisting of:
coherent;
and
coherent and collimated.

3. The method of claim 1, further comprising forming the first beam of radiation in a vertical line.

4. The method of claim 1, further comprising measuring a width of at least one captured beam of radiation.

5. The method of claim 1, wherein the determination of the presence of one or more interferents comprises:
measuring an amount of lipemia in a serum or plasma portion of the clinical analysis specimen based upon the analyzing the first captured beam of radiation.

6. The method of claim 1, wherein the determination of the presence of one or more interferents comprises:
measuring an amount of hemolysis in a serum or plasma portion of the clinical analysis specimen.

7. The method of claim 1, wherein the determination of the presence of one or more interferents comprises:
measuring an amount of icterus in a serum or plasma portion of the clinical analysis specimen.

8. A method for determining a characteristic of a clinical analysis specimen contained within a sample container, comprising:
orienting the sample container until a view window in the sample container is displayed, wherein the sample container is in an upright position and has a label provided thereon, the view window provided where the label is not located;
transmitting a first beam of radiation comprising a collimated light source from a first radiation source and a second beam of radiation from a second radiation source comprising a white light source through the sample container wherein the first beam and second beam are transmitted onto a first side and second side of the sample container, respectively, the second beam nonparallel with the first beam;
capturing respective beams of radiation transmitted through the sample container via a first radiation capture device and a second radiation capture device wherein the first radiation capture device and the second radiation capture device are located on sides of the sample container opposite the first side and the second side, respectively; and
analyzing one captured beam of radiation from the first radiation source to determine a physical dimensional characteristic of the clinical analysis specimen; and
analyzing another captured beam of radiation from the second radiation source to determine a presence of one or more interferents in an endogenous state within the clinical analysis specimen.

9. The method of claim 8, wherein determining the physical dimensional characteristic of the clinical analysis specimen comprises one or more steps selected from a group consisting of:
determining a location of an interface (SR) between a serum or plasma portion and a red blood cell portion of the clinical analysis specimen that has been centrifuged;
determining a location of an interface (SSR) between a red blood cell portion and a serum separator portion of the clinical analysis specimen that has been centrifuged; and
determining a location of an interface (SS) between a serum or plasma portion and a serum separator portion of the clinical analysis specimen that has been centrifuged.

10. A method for determining a characteristic, comprising:
orienting a sample container until a view window in the sample container is displayed, wherein the sample container is in an upright position and has a label provided thereon, the view window provided where the label is not located;
transmitting a first beam of radiation from a first radiation source comprising a collimated light source and a second beam of radiation from a second radiation source comprising a white light source through the sample container adapted to contain a clinical analysis specimen wherein the first beam and second beam are transmitted onto a first side and second side of the sample container, respectively, the second beam nonparallel with the first beam;
capturing respective beams of radiation transmitted through the sample container via a first radiation capture device and a second radiation capture device wherein the first radiation capture device and the second radiation capture device are located on sides of the sample container opposite the first side and the second side, respectively; and
analyzing one captured beam of radiation from the first radiation source to determine a physical dimensional characteristic of the sample container; and
analyzing another captured beam of radiation from the white light source to determine a presence of one or more interferents in an endogenous state within the clinical analysis specimen.

11. The method of claim 10, wherein determining the physical dimensional characteristic of the sample container comprises one or more steps selected from a group consisting of:
determining a location of a tube-cap interface (TC) of the sample container; and
determining a height or width of the sample container.

12. An apparatus adapted to determine a characteristic of a clinical analysis specimen contained within a sample container, comprising:
a rotating holder integrated with the apparatus to hold and rotate the sample container until a view window within the sample container is displayed, wherein the sample container is in an upright position and has a label provided thereon, the view window provided where the label is not located;
a first radiation source comprising a collimated light source adapted to transmit a first beam and second radiation source comprising a white light source adapted to transmit a second beam of radiation through the clinical analysis specimen contained within the sample container wherein the first beam and second beam are transmitted onto a first side and second side of the sample container, respectively, wherein a first beam of radiation from the first radiation source is nonparallel with a beam of radiation from the second radiation source;

a first radiation capture device adapted to capture a first captured beam of radiation and a second radiation capture device adapted to capture a second captured beam of radiation as transmitted through the sample container wherein the first radiation capture device and second radiation capture device are located on sides of the sample container opposite the first side and the second side, respectively; and a computer adapted to analyze the first captured beam of radiation and the second captured beam of radiation to determine a presence of one or more interferents in an endogenous state within the clinical analysis specimen, and adapted to analyze the first captured beam to determine a physical dimensional characteristic of the sample container or a physical dimensional characteristic of the clinical analysis specimen.

13. The apparatus of claim 12, wherein the first radiation source is a source of coherent radiation.

14. The apparatus of claim 12, wherein the first radiation source is a source of collimated radiation.

15. The apparatus of claim 12, wherein the one or more interferents is selected from a group consisting of:
lipemia;
hemolysis; and
icterus.

16. A method to determine a characteristic of a clinical analysis specimen contained within a sample container, comprising:
orienting the sample container until a view window in the sample container is displayed, wherein the sample container is in an upright position and has a label provided thereon, the view window provided where the label is not located;
transmitting a first beam of radiation from a first radiation source comprising a collimated light source and a second beam of radiation from a second radiation source comprising a white light source onto a first side of the clinical analysis specimen contained within the sample container;
capturing a first captured beam of radiation as the first beam reflected by or passing through the clinical analysis specimen via a radiation capture device;
capturing a second captured beam of radiation as the second beam reflected by the clinical analysis specimen via the radiation capture device;
analyzing the first captured beam of radiation to determine a physical dimensional characteristic of the clinical analysis specimen or of the sample container; and
analyzing the second captured beam of radiation to determine a presence of one or more interferents in an endogenous state within the clinical analysis specimen.

17. The method of claim 16, wherein the first beam of radiation is coherent.

18. The method of claim 16, wherein the first beam of radiation is collimated.

19. The method of claim 16, further comprising projecting the first beam of radiation in a vector rotationally offset from a vector aligned between the sample container and the radiation capture device capturing the first captured beam and the second captured beam of radiation, wherein the first radiation source and the radiation capture device.

20. A method to determine a characteristic of a clinical analysis specimen contained within a sample container, comprising:
orienting the sample container until a view window in the sample container is displayed, wherein the sample container is in an upright position and has a label provided thereon, the view window provided where the label is not located;
transmitting a first beam of radiation comprising a coherent radiation from a first radiation source and a second beam of radiation comprising white light radiation from a second radiation source onto a first side of the sample container;
capturing one beam of radiation reflected by or passing through the clinical analysis specimen in the sample container via a radiation capture device;
capturing another beam of radiation reflected by the clinical analysis specimen in the sample container via a the radiation capture device;
analyzing the one beam of radiation to determine a physical dimensional characteristic of the clinical analysis specimen or a physical dimensional characteristic of the sample container; and
analyzing the another beam of radiation to determine a presence of an interferent in an endogenous state within the clinical analysis specimen.

21. An apparatus for analyzing a clinical analysis specimen contained within a sample container, comprising:
a rotating holder integrated with the apparatus to hold and rotate the sample container until a view window within the sample container is displayed, wherein the sample container is in an upright position and has a label provided thereon, the view window provided where the label is not located;
a first radiation source comprising coherent radiation adapted to transmit a first beam onto a first side of the clinical analysis specimen contained within the sample container and a second radiation source comprising white light radiation adapted to transmit a second beam onto the first side of the clinical analysis specimen contained within the sample container;
a radiation capture device positioned to capture a first captured beam of the first beam of coherent radiation reflected by or passing through the sample container and a second captured beam of white light radiation reflected by the clinical analysis specimen in the sample container; and
a computer adapted to analyze the first captured beam of radiation to determine a physical dimensional characteristic of the clinical analysis specimen or of the sample container, and analyze the second captured beam of radiation to determine a presence of one or more interferents in an endogenous state within the clinical analysis specimen.

* * * * *